US012605249B2

(12) United States Patent
Yakobson et al.

(10) Patent No.: US 12,605,249 B2
(45) Date of Patent: Apr. 21, 2026

(54) IMPLANTABLE ELECTROMAGNETIC FIELD GENERATOR FOR ORTHOPEDIC THERAPY

(71) Applicant: Pulsar Medtech Ltd., Bnei-Brak (IL)

(72) Inventors: Elad Yakobson, Tel-Aviv (IL); Shlomo Barak, Tel-Aviv (IL)

(73) Assignee: Pulsar Medtech Ltd., Bnei-Brak (IL)

( * ) Notice: Subject to any disclaimer, the term of this patent is extended or adjusted under 35 U.S.C. 154(b) by 790 days.

(21) Appl. No.: 17/430,779

(22) PCT Filed: Feb. 13, 2020

(86) PCT No.: PCT/IL2020/050169
§ 371 (c)(1),
(2) Date: Aug. 13, 2021

(87) PCT Pub. No.: WO2020/165905
PCT Pub. Date: Aug. 20, 2020

(65) Prior Publication Data
US 2022/0133478 A1      May 5, 2022

Related U.S. Application Data

(60) Provisional application No. 62/804,769, filed on Feb. 13, 2019.

(51) Int. Cl.
*A61F 2/28*        (2006.01)
*A61F 2/08*        (2006.01)
(Continued)

(52) U.S. Cl.
CPC .............. *A61F 2/28* (2013.01); *A61F 2/0811* (2013.01); *A61N 2/004* (2013.01); *A61N 2/02* (2013.01);
(Continued)

(58) Field of Classification Search
CPC .. A61F 2/28; A61F 2/0811; A61F 2002/0852; A61F 2002/2821; A61N 2/004; A61N 2/02
See application file for complete search history.

(56) References Cited

U.S. PATENT DOCUMENTS 9,327,115 B2     5/2016  Neuman et al.
9,776,014 B2    10/2017  Neuman et al.
(Continued)

FOREIGN PATENT DOCUMENTS

CN        101431956      5/2009
CN        102905630      1/2013
(Continued)

OTHER PUBLICATIONS

International Preliminary Report on Patentability Dated May 26, 2020 From the International Bureau of WIPO Re. Application No. PCT/IL2020/050169. (8 Pages).
(Continued)

*Primary Examiner* — Brooke Labranche

(57)        ABSTRACT

An anchor for attaching injured soft tissue to a bone and generating a therapeutic electromagnetic field at least in a part of the soft tissue when the soft tissue is sutured to the anchor, the anchor comprising:
  a) an affixing portion configured for affixing the anchor to the bone;
  b) a coil that generates the electromagnetic field when a current runs through it;
  c) an electronics module that controls the current in the coil; and
  d) an electric power source that provides electric power to the electronics module and the coil.

31 Claims, 23 Drawing Sheets

(51) Int. Cl.
    *A61N 2/00*          (2006.01)
    *A61N 2/02*          (2006.01)
(52) U.S. Cl.
    CPC ................. *A61F 2002/0852* (2013.01); *A61F*
                                *2002/2821* (2013.01)

(56) References Cited

U.S. PATENT DOCUMENTS

| | | | |
|---|---|---|---|
| 10,238,867 | B2 | 3/2019 | Ryaby et al. |
| 10,376,708 | B2 | 8/2019 | Neuman et al. |
| 2008/0027470 | A1 | 1/2008 | Hart et al. |
| 2010/0030011 | A1 | 2/2010 | Weadock et al. |
| 2010/0036416 | A1 | 2/2010 | Martin |
| 2010/0211174 | A1 | 8/2010 | Scarborough |
| 2010/0292756 | A1* | 11/2010 | Schneider .............. A61N 1/326 |
| | | | 607/50 |
| 2010/0298886 | A1* | 11/2010 | Kraus ................ A61B 5/14539 |
| | | | 606/301 |
| 2012/0215281 | A1 | 8/2012 | Neuman |
| 2013/0165733 | A1* | 6/2013 | Rogachefsky ......... A61B 17/80 |
| | | | 600/12 |
| 2013/0267998 | A1 | 10/2013 | Vijay et al. |
| 2013/0310628 | A1 | 11/2013 | Chisena et al. |
| 2014/0088717 | A1 | 3/2014 | Boyden et al. |
| 2014/0220509 | A1* | 8/2014 | Vladila ................ A61C 8/0006 |
| | | | 600/9 |
| 2014/0342428 | A1 | 11/2014 | Goodwin et al. |
| 2015/0127048 | A1 | 5/2015 | Curtis |

FOREIGN PATENT DOCUMENTS

| | | |
|---|---|---|
| CN | 104487004 | 4/2015 |
| WO | WO 2011/051947 | 5/2011 |
| WO | WO 2012/093277 | 7/2012 |
| WO | WO 2013/101962 | 7/2013 |
| WO | WO 2019/142196 | 7/2019 |
| WO | WO 2020/165905 | 8/2020 |

OTHER PUBLICATIONS

International Search Report and the Written Opinion Dated May 6, 2020 From the International Searching Authority Re. Application No. PCT/IL2020/050169. (15 Pages).

Binder et al. "Pulsed Electromagnetic Field Therapy of Persistent Rotator Cuff Tendinitis. A Double-Blind Controlled Assessment", The Lancet, 1(8379): 695-698, Mar. 31, 1984.

Castagna et al. "Comparative Cost-Effectiveness Analysis of the Subacriomal Spacer for Irreparable and Massive Totator Cuff Tears", International Orthopaedics, 43(2): 395-403, Published Online Jul. 31, 2018.

De Girolamo et al. "In Vitro Functional Response of Human Tendon Cells to Different Dosages of Low-Frequency Pulsed Electromagnetic Field", Knee Surgery, Sports Traumatology, Arthroscopy, 23(11): 3443-3453, Published Online Jun. 24, 2014.

Denaro et al. "Effect of Pulsed Electromagnetic Fields on Human Tenocyte Cultures From Supraspinatus and Quadriceps Tendons", American Journal of Physical Medicine & Rehabilitation, 90(2): 119-127, Feb. 2011.

Dolkart et al. "Effects of Focused Continues Pulsed Electromagnetic Field Therapy on Early Tendon-to-Bone Healing: Rat Supraspinatus Detachment and Repair Model", Bone & Joint Research, 10(5): 298-306, May 2021.

Huegel et al. "Effects of Pulsed Electromagnetic Field Therapy at Different Frequencies and Durations on Rotator Cuff Tendon-to-Bone Healing in A Rat Model", Journal of Shoulder and Elbow Surgery, 27(3): 553-560, Published Online Nov. 22, 2017.

Huegel et al. "Effects of Pulsed Electromagnetic Field Therapy on Rat Achilles Tendon Healing", Journal of Orthopaedic Research, 38(1): 70-81, Published Online Oct. 15, 2019.

Ibiwoye et al. "Bone Mass Is Preserved in A Critical-Sized Osteotomy by Low Energy Pulsed Electromagnetic Fields as Quantitated by In Vivo Micro-Computed Tomography", Journal of Orthopaedic Research, 22(5): 1086-1093, Sep. 2004.

Liu et al. "Role of Pulsed Electromagnetic Fields (PEMF) on Tenocytes and Myoblasts—Potential Application for Treating Rotator Cuff Tears", Journal of Orthopaedic Research, 35(5): 956-964, Published Online Apr. 7, 2017.

Magnoni Moretto Nunes et al. "Evaluation of Pulsed Electromagnetic Field in Protocols in Implant Osseointegration: In Vivo and In Vitro Study", Clinical Oral Investigations, 25(5): 2925-2937, Published Online Oct. 9, 2020.

Marmotti et al. "Pulsed Electromagnetic Fields Improve Tenogenic Commitment of Umbilical Cord-Derived Mesenchymal Stem Cells: A Potential Strategy for Tendon Repair—An In Vitro Study", Stem Cells International, 2018(Art.ID 9048234): 1-19, Jul. 30, 2018.

Midura et al. "Pulsed Electromagnetic Field Treatments Enhance the Healing of Fibular Osteotomies", Journal of Orthopaedic Research, 23(5): 1035-1046, Sep. 2005.

Osti et al. "Pulsed Electromagnetic Fields After Rotator Cuff Repair: A Randomized, Controlled Study", Orthopedics, 38(3): e223-e228, Mar. 2015.

Page et al. "Electrotherapy Modalities for Rotator Cuff Disease (Review)", Cochrane Database of Systematic Reviews, 6(CD012225): 1-220, Jun. 10, 2016.

Patterson et al. "Exposure of Murine Cells to Pulsed Electromagnetic Fields Rapidly Activates the mTOR Signaling Pathway", Biooelectromagnetics, 27(7): 535-544, Published Online May 19, 2006.

Perucca Orfel et al. "Pulsed Electromagnetic Fields Improve the Healing Process of Achilles Tendinopathy. A Pilot Study in A Rat Model", Bone & Joint Research, 9(9): 613-622, Sep. 2020.

Randelli et al. "Effects of the Pulsed Electromagnetic Field PST® on Human Tendon Stem Cells: A Controlled Laboratory Study", BMC Complementary and Alternative Medicine, 16(1): 293-1-293-11, Aug. 18, 2016.

Rossi et al. "Current Concepts in Rotator Cuff Repair Techniques: Biomechanical, Functional, and Structural Outcomes", The Orthopaedic Journal of Sports Medicine, 7(9): 2325967119868674-1 2325967119868674-8, Sep. 20, 2019.

Rosso et al. "Mechanical Stimulation (Pulsed Electromagnetic Fields 'PEMF' and Extracorporeal Shock Wave Therapy 'ESWT') and Tendon Regeneration: A Possible Alternative", Frontiers in Aging Neuroscience, 7(Art.211): 1-11, Nov. 9, 2015.

Sabesan et al. "Factors Affecting the Cost and Profitability of Arthroscopic Rotator Cuff Repair", Arthroscopy, 35(1): 38-42, Published Online Nov. 22, 2018.

Sakai et al. "Exposure of Mouse Preosteoblasts to Pulsed Electromagnetic Fields Reduces the Amount of Mature, Type I Collagen in the Extracellular Matrix", Journal of Orthopaedic Research, 24(2): 242-253, Feb. 2006.

Saliev et al. "Therapeutic Potential of Electromagnetic Fields for Tissue Enginccring and Wound Healing", Cell Proliferation, 47(6): 485-493, Published Online Oct. 16, 2014.

Thigpen et al. "The American Society of Shoulder and Elbow Therapists' Consensus Statement on Rehabilitation Following Arthroscopic Rotator Cuff Repair", Journal of Shoulder and Elbow Surgery, 25(4): 521-535, Apr. 2016.

Tucker et al. "Pulsed Electromagnetic Field Therapy Improves Tendon-to-Bone Healing in A Rat Rotator Cuff Repair Model", Journal of Orthopaedic Research, 35(4): 902-909, Published Online Jun. 22, 2016.

Zborowski et al. "Decibel Attenuation of Pulsed Electromagnetic Field (PEMF) in Blood and Cortical Bone Determined Experimentally and From the Theory of Ohmic Losses", Annals of Biomedical Engineering, 34(6): 1030-1041, Published Online May 18, 2006.

Zborowski et al. "Magnetic Field Visualization in Applications to Pulsed Electromagnetic Field Stimulation of Tissues", Annals of Biomedical Engineering, 31(2): 195-206, Feb. 2003.

Notification of Office Action and Search Report Dated Jan. 26, 2024 From the National Intellectual Property Administration of the People's Republic of China Re. Application No. 202080028425.7. (6 Pages).

(56) References Cited

OTHER PUBLICATIONS

English Summary and Translation Dated Feb. 8, 2024 of Notification of Office Action Dated Jan. 26, 2024 From the National Intellectual Property Administration of the People's Republic of China Re. Application No. 202080028425.7. (2 Pages).

Decision on Rejection Dated Aug. 2, 2024 From the State Intellectual Property Office of the People's Republic of China Re. Application No. 202080028425.7 and Its Machine Translation Into English. (12 Pages).

English Summary Dated Aug. 28, 2024 of Decision on Rejection Dated Aug. 2, 2024 From the State Intellectual Property Office of the People's Republic of China Re. Application No. 202080028425.7 (3 Pages).

English Summary Dated Jun. 11, 2024 of Notification of Office Action and Search Report Dated May 29, 2024 From the National Intellectual Property Administration of the People's Republic of China Re. Application No. 202080028425.7 (4 Pages).

Notification of Office Action and Search Report Dated May 29, 2024 From the National Intellectual Property Administration of the People's Republic of China Re. Application No. 202080028425.7 and Its Machine Translation Into English. (13 Pages).

* cited by examiner

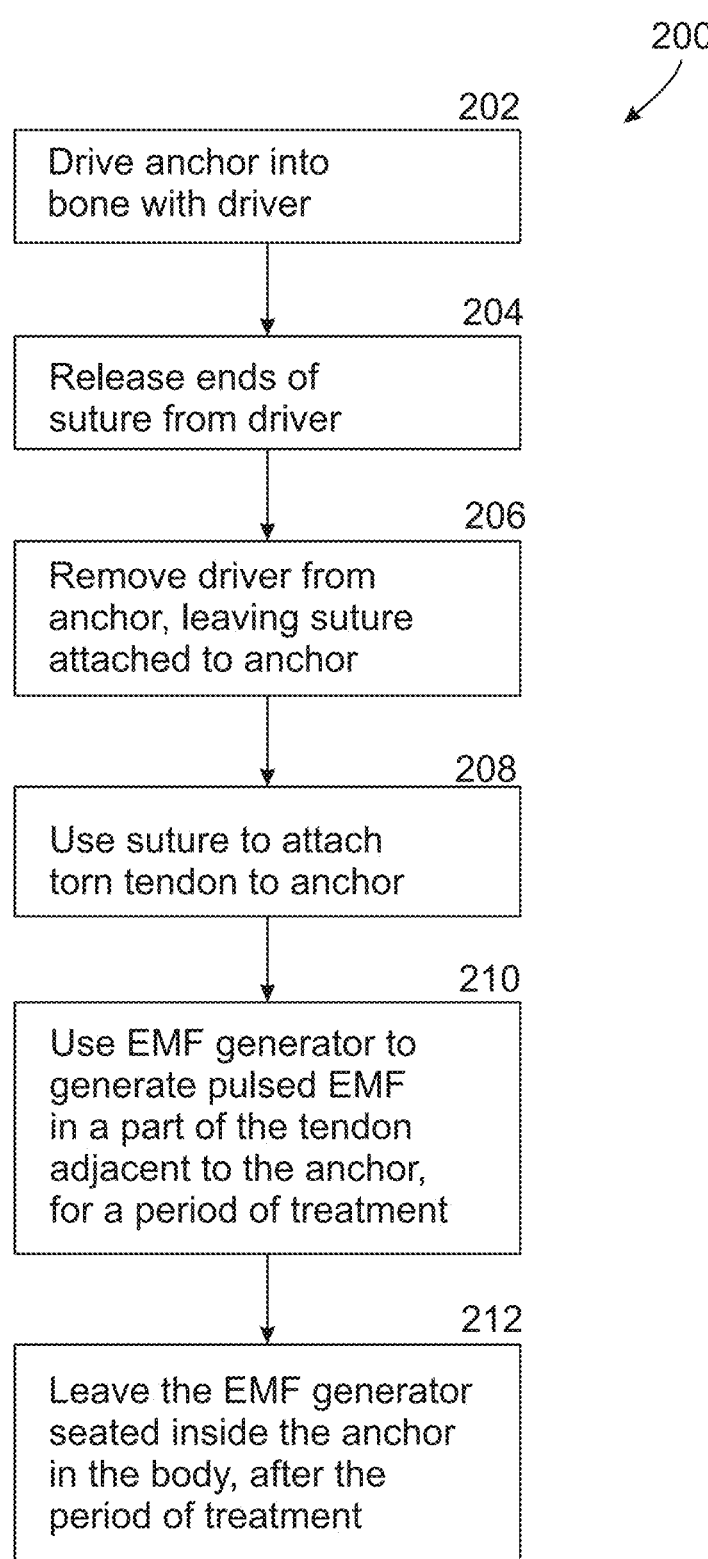

200

202

Drive anchor into
bone with driver

204

Release ends of
suture from driver

206

Remove driver from
anchor, leaving suture
attached to anchor

208

Use suture to attach
torn tendon to anchor

210

Use EMF generator to
generate pulsed EMF
in a part of the tendon
adjacent to the anchor,
for a period of treatment

212

Leave the EMF generator
seated inside the anchor
in the body, after the
period of treatment

FIG. 2

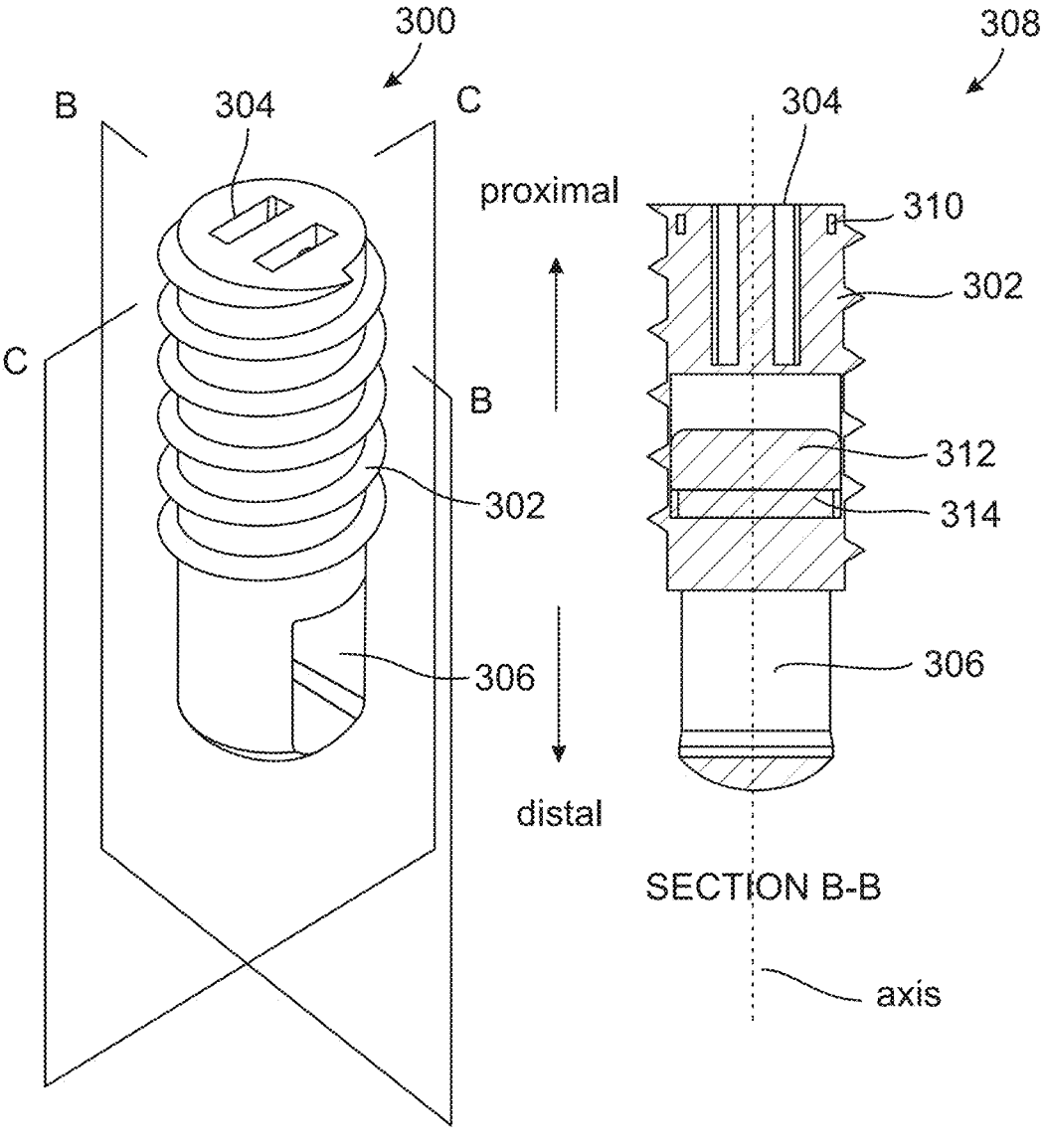
FIG. 3A                    FIG. 3B

316

318 proximal

310

302

312

314

306 distal

SECTION C-C

320

304

302

310

TOP
(proximal end)

322

324          328          326

A

CLOSEUP A          330

328

IMPLANTABLE ELECTROMAGNETIC FIELD GENERATOR FOR ORTHOPEDIC THERAPY

RELATED APPLICATIONS

This application is a National Phase of PCT Patent Application No. PCT/IL2020/050169 having International filing date of Feb. 13, 2020, which claims the benefit of priority under 35 USC § 119 (e) of U.S. Provisional Patent Application No. 62/804,769 filed on Feb. 13, 2019. The contents of the above applications are all incorporated by reference as if fully set forth herein in their entirety.

FIELD AND BACKGROUND OF THE INVENTION

The present invention, in some embodiments thereof, relates to a system to promote faster and/or more complete orthopedic healing and, more particularly, but not exclusively, to a system to speed tendon to bone healing especially of a rotator cuff.

Rotator cuff (RC) tears are common musculoskeletal injuries which often require surgical intervention. Unfortunately, surgical repairs fail in many cases. In some cases, repaired tissue may be fibrotic, disorganized and/or reattach poorly to the bony insertion.

Published U.S. Patent Application Publication Nos. US2008/0027470 to Hart et al, and US2010/0211174 to Scarborough, describe methods of treating rotator cuff injuries by reattaching the tendon to the bone.

U.S. Pat. Nos. 9,327,115, 9,776,014, and 10,376,708, all to Neuman et al, describe a method of osteointegration of a dental implant into surrounding jaw-bone, the method comprising applying a magnetic field around the implant, the magnetic field produced by a coil within the implant. A device adapted for insertion into a jawbone implant and for producing the magnetic field for bone enhancement of surrounding jaw-bone is also described.

International Patent Application Publication No. WO 2019/142196 to Yakobson et al, describes an electronic skin patch for stimulating tissue healing at a target site, which includes a capacitor in series with a coil, through which pulses of current flow to produce an electromagnetic field at the target site during each pulse period. Most of the electromagnetic field energy of the coil comes from the capacitor at the beginning of the pulse period and returns to the capacitor at the end of the pulse period.

U.S. Pat. No. 10,238,867 to Ryaby et al describes a pulsed electromagnetic field (PEMF) device for musculoskeletal tissue stimulation. The PEMF device includes sensors that detect attributes indicating whether the PEMF device is in use. The PEMF device also includes communication devices that connect it to other devices. The data obtained from the sensors may be used to determine a level of compliance in use of the device with a prescribed treatment regimen for the patient.

Huegel et al, "Effects of pulsed electromagnetic field therapy at different frequencies and durations on rotator cuff tendon-to-bone healing in a rat model," *J. Shoulder Elbow Surg.* 27, 553-560 (2018), describes a study to determine the influence of both PEMF frequency and exposure time on rotator cuff healing.

SUMMARY OF THE INVENTION

An aspect of some embodiments of the invention concerns a suture anchor for reattaching a torn tendon to a bone, with an electromagnetic field generator inside that can produce therapeutic electromagnetic fields in the part of the tendon that is sutured to the anchor, to promote healing.

There is thus provided, in accordance with an exemplary embodiment of the invention, an anchor for attaching injured soft tissue to a bone and generating a therapeutic electromagnetic field at least in a part of the soft tissue when the soft tissue is sutured to the anchor, the anchor comprising:

a) an affixing portion configured for affixing the anchor to the bone;
 b) a coil that generates the electromagnetic field when a current runs through it;
 c) an electronics module that controls the current in the coil; and
 d) an electric power source that provides electric power to the electronics module and the coil.

Optionally, the affixing portion is threaded, and affixes the anchor to the bone by screwing into the bone.

Optionally, the anchor comprises a fitting into which or around which a driving tool can be inserted, to screw the affixing portion into the bone.

Optionally, the anchor comprises one or more eyelets for attaching a suture to the anchor.

Optionally, the anchor is configured to attach to the bone by penetrating at least partly into the bone in an axial direction of the anchor.

Optionally, most of a conductor volume of the coil is located within 2 mm in the axial direction of a proximal end of the anchor.

Optionally, a proximal part of the anchor is substantially circular cylindrical, aside from any threads for screwing it into the bone, and the coil extends over an area perpendicular to the axial direction that is at least 50% of the circular cross-sectional area of the proximal part of the anchor.

Optionally, the coil, when it has current running in it, has a direction of magnetic moment oriented within 20 degrees of the axial direction.

Optionally, an effective length of the coil, defined as twice a standard deviation of a distribution of conductor along the direction of magnetic moment, is less than an effective diameter, defined as a maximum extent of conductor in a direction perpendicular to the direction of the magnetic moment.

Optionally, the electronics module is configured to cause enough current to pass through the coil to produce a magnetic field of at least 0.5 millitesla, in at least one location at least 1 mm in an axial direction beyond a proximal end of the anchor.

Optionally, the anchor comprises one or more eyelets for attaching a suture to the anchor, at least one eyelet located distal to the coil, or passing through the coil.

Optionally, the electronics module is configured to cause the current to run through the coil, for a series of pulse times shorter than 300 microseconds, with a waiting period following each pulse time that is at least 100 times longer than the pulse time, with the current during the waiting period sufficiently low so that the total energy dissipated by the current during the waiting time is less than the total energy dissipated by the current during the pulse time.

Optionally, the electronics module is configured to cause the current running through the coil during each pulse time to be substantially one cycle of a sine wave.

Optionally, the electronics module comprises a capacitor, and the electronics module is configured to cause most of the maximum electromagnetic field energy of the coil during each pulse time to go to electric field energy of the capacitor and to remain there during the following waiting period, and to return back to electromagnetic field energy of the coil during the next pulse time.

Optionally, the electric power source comprises one or more batteries.

Optionally, the coil, the electronics module and the electric power source are sealed inside the anchor.

Optionally, the anchor also comprises at least one suture attached to the anchor.

Optionally, the coil is comprised in the suture.

Optionally, the suture passes from an opening in a proximal surface of the anchor, between two or more batteries or through a hole in one battery, through an eyelet distal to the battery or batteries, back between two or more batteries or through a hole in one battery, and back through an opening in the proximal surface of the anchor.

There is further provided, in accordance with an exemplary embodiment of the invention, a method of treating a patient with an injured soft tissue, comprising:
   a) affixing to a bone of the patient a suture anchor comprising an electromagnetic field generator encased in the anchor;
   b) suturing the soft tissue to the anchor; and
   c) using the electromagnetic field generator to generate therapeutic electromagnetic fields at least in a part of the soft tissue adjacent to the anchor for at least one day.

Optionally, the method comprises:
   a) continuing to generate the electromagnetic fields for a period of time and then stopping; and
   b) leaving the anchor inside the patient's body for at least a year after stopping.

Optionally, affixing the suture anchor to the bone comprises screwing the anchor into the bone using a driving tool inserted into a fitting in the anchor.

Optionally, affixing the suture anchor to the bone comprises punching the anchor into the bone.

Optionally, the method comprises using the electromagnetic field generator to generate pulsed therapeutic electromagnetic fields in the torn tendon, with waiting times between the pulses that are at least 100 times as long as the pulses.

Optionally, the electromagnetic field during each pulse is substantially a sawtooth wave.

Alternatively, the electromagnetic field during each pulse is substantially one cycle of a sine wave.

Optionally, generating the pulsed electromagnetic field comprises:
   a) recovering most of the electromagnetic field energy from each pulse and storing it in a capacitor comprised in the electromagnetic field generator; and
   b) using most of the stored energy to generate the next pulse.

Optionally, the peak magnetic field within each pulse is at least 0.2 mT everywhere within 1 mm of a proximal end of the anchor in the proximal direction, and within 2 mm of a longitudinal axis of the anchor.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2 is a flowchart for a method of using the suture anchor described in FIG. 1B, for treating a torn tendon, according to an exemplary embodiment of the invention;

Figures 3C, 3D, 3E:
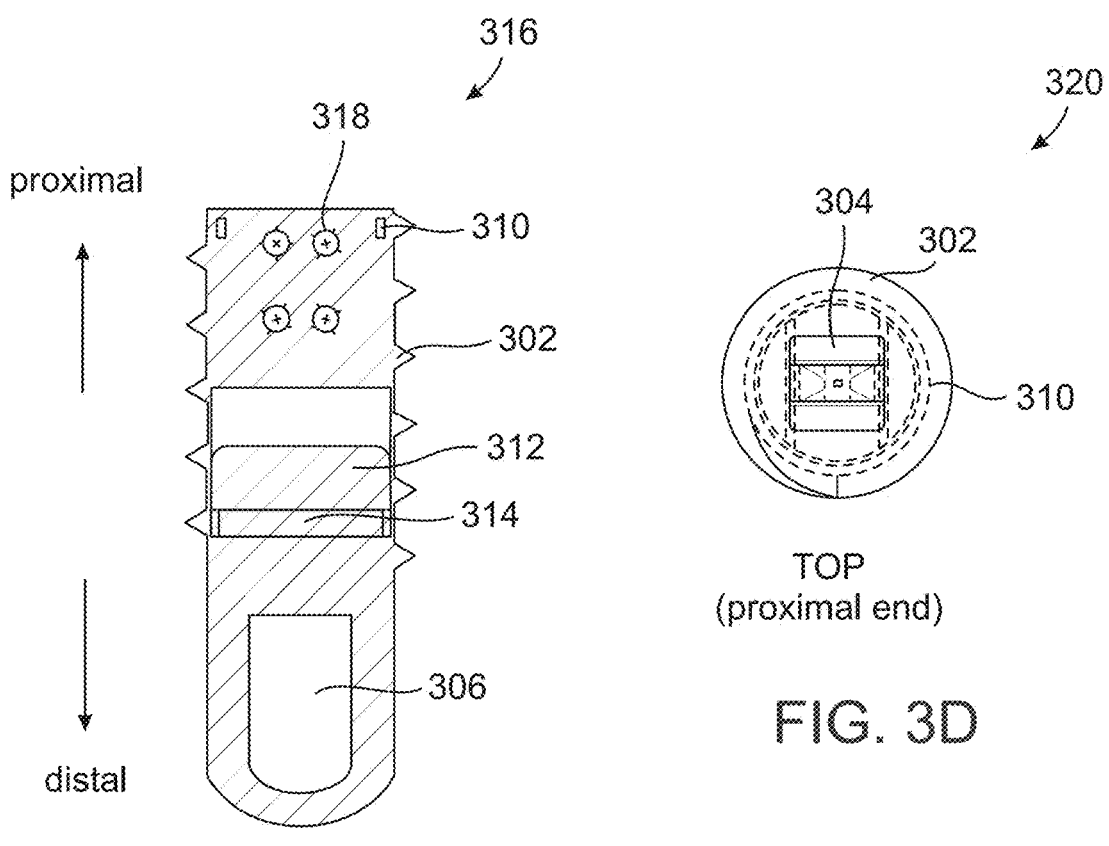
Figure 4A:
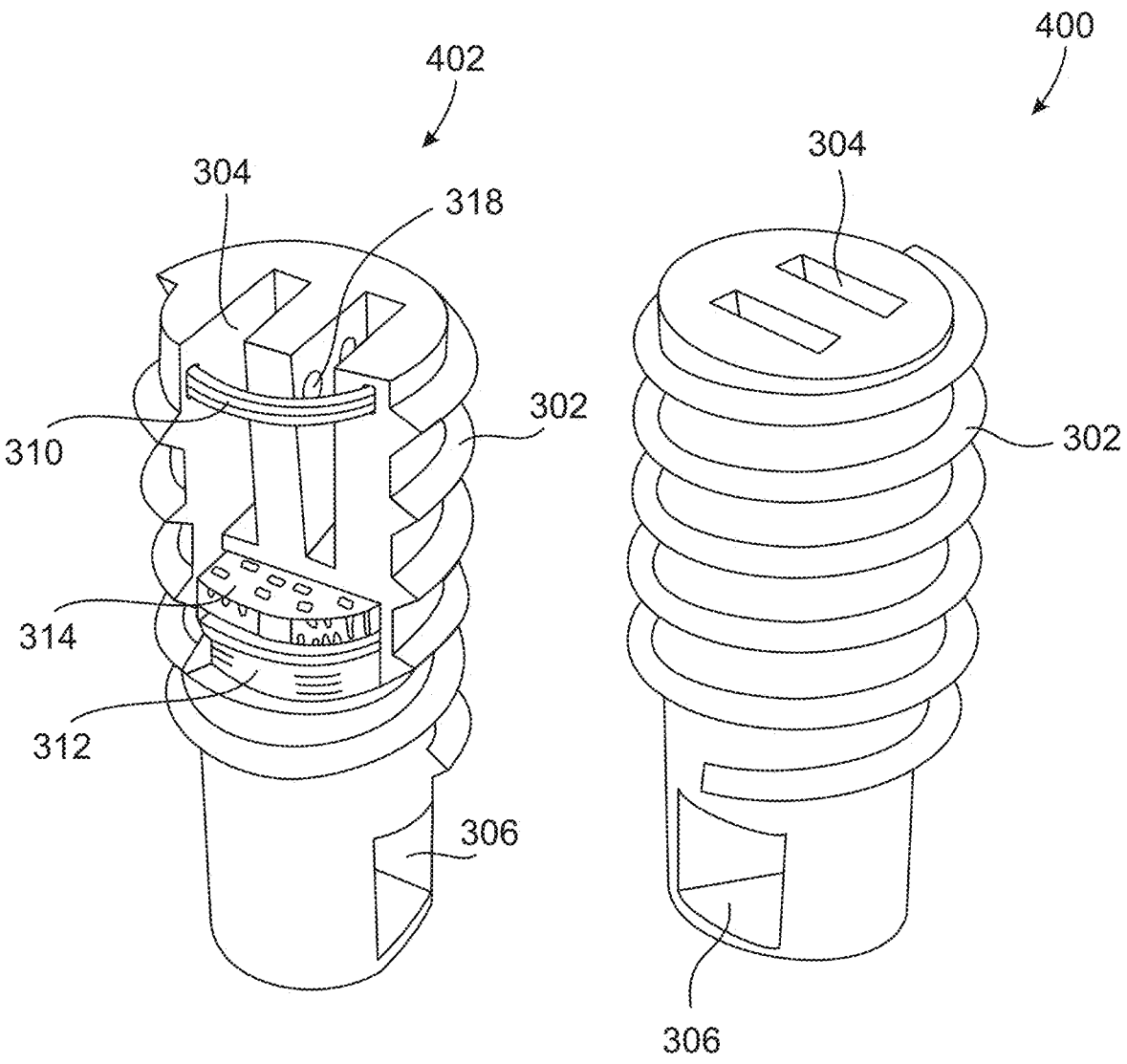
Figure 4B:
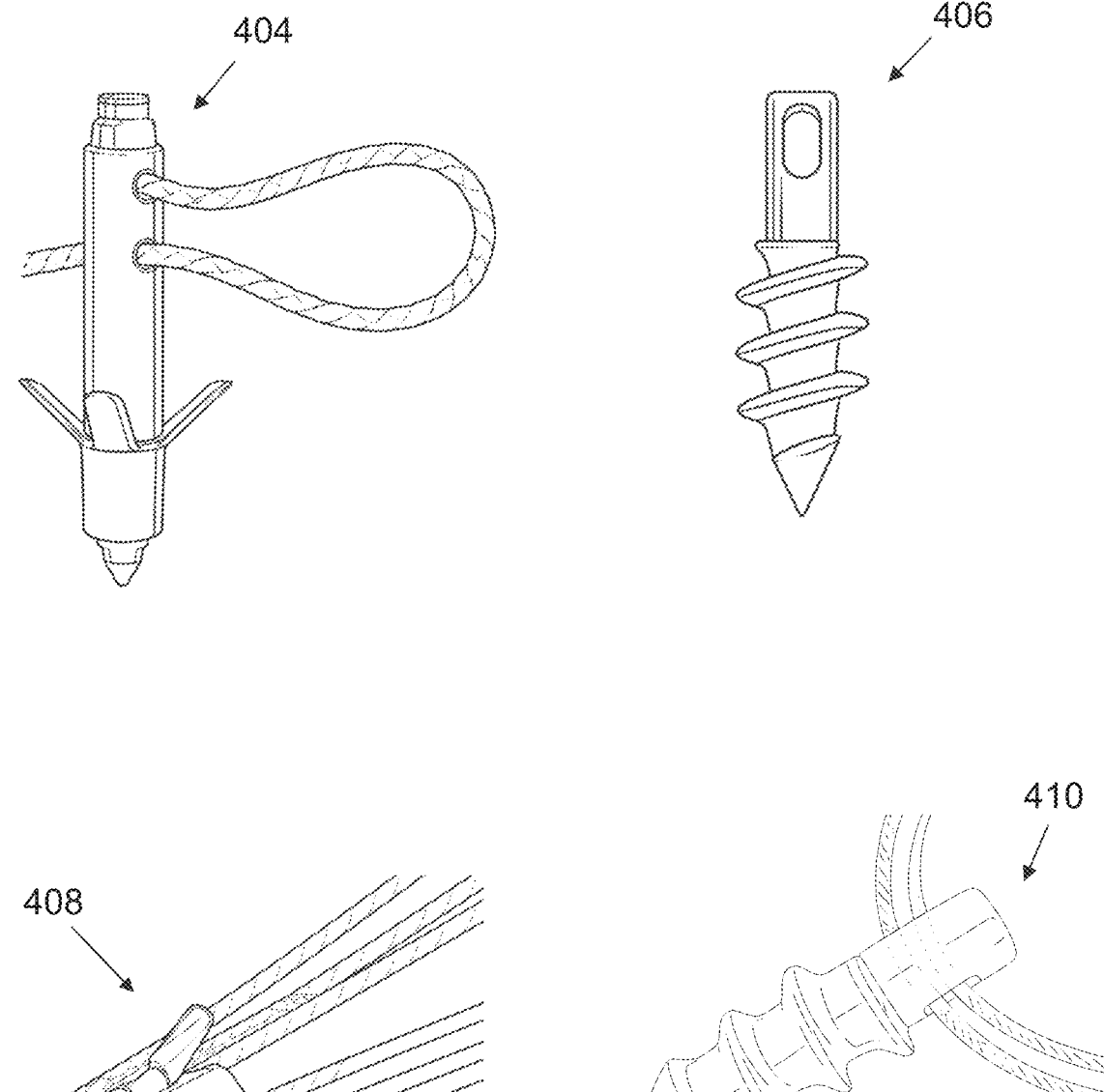
Figure 4C:
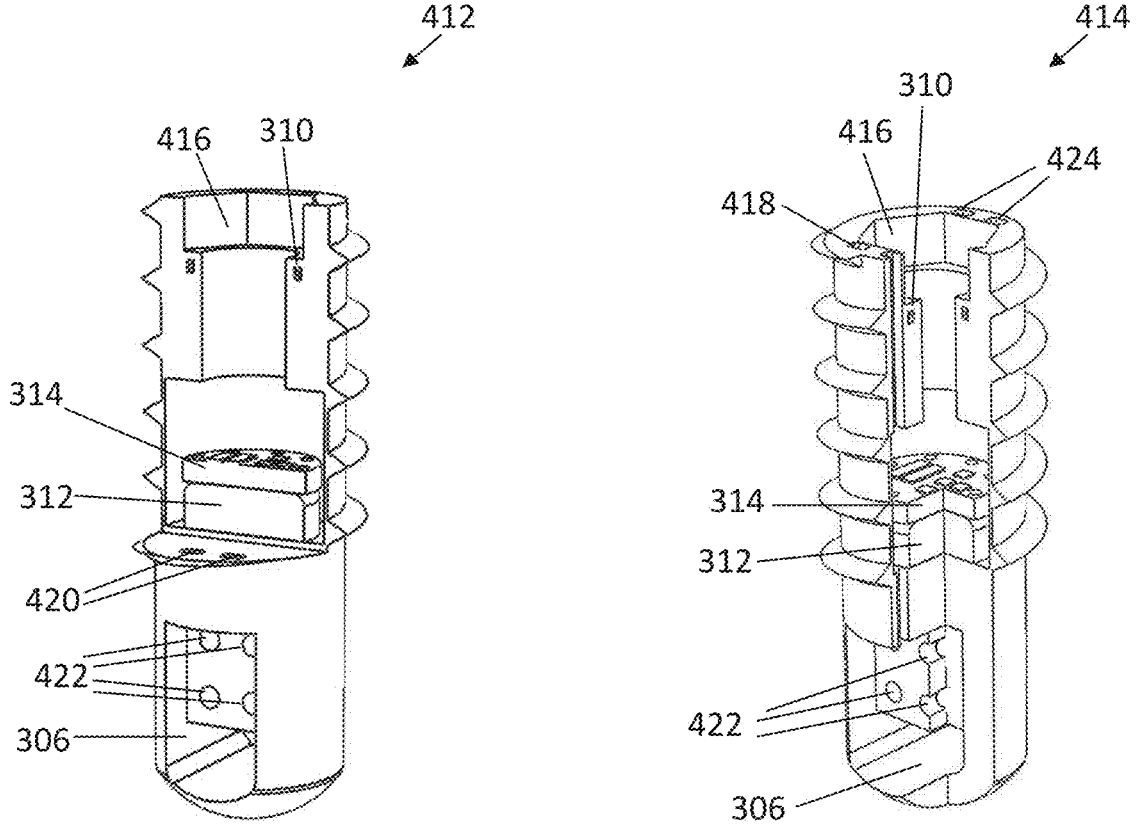
Figure 4D:
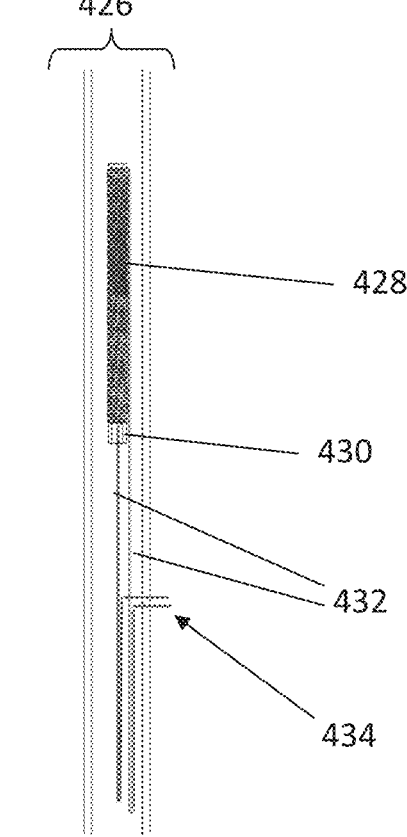
Figure 5:
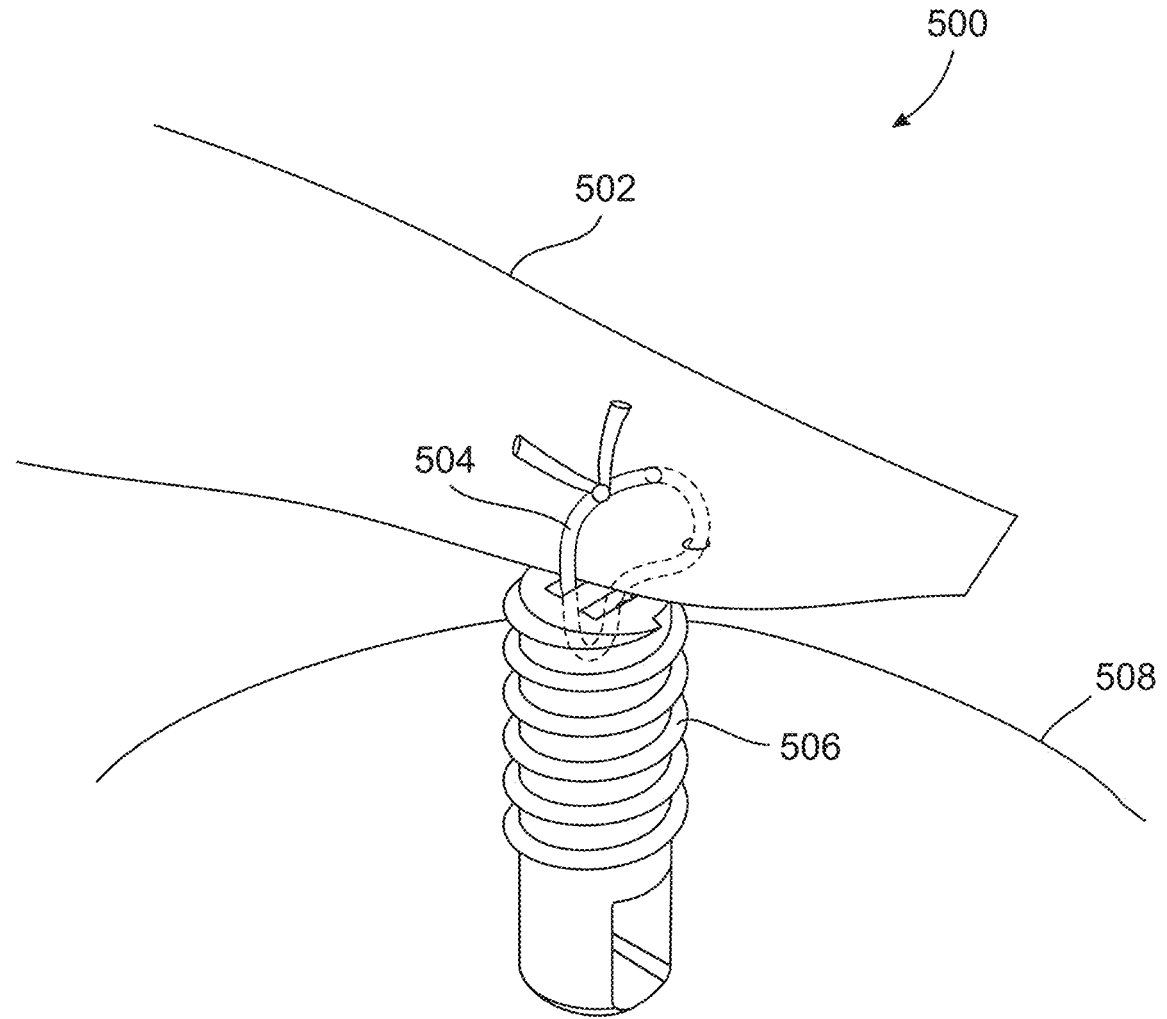
Figure 6:
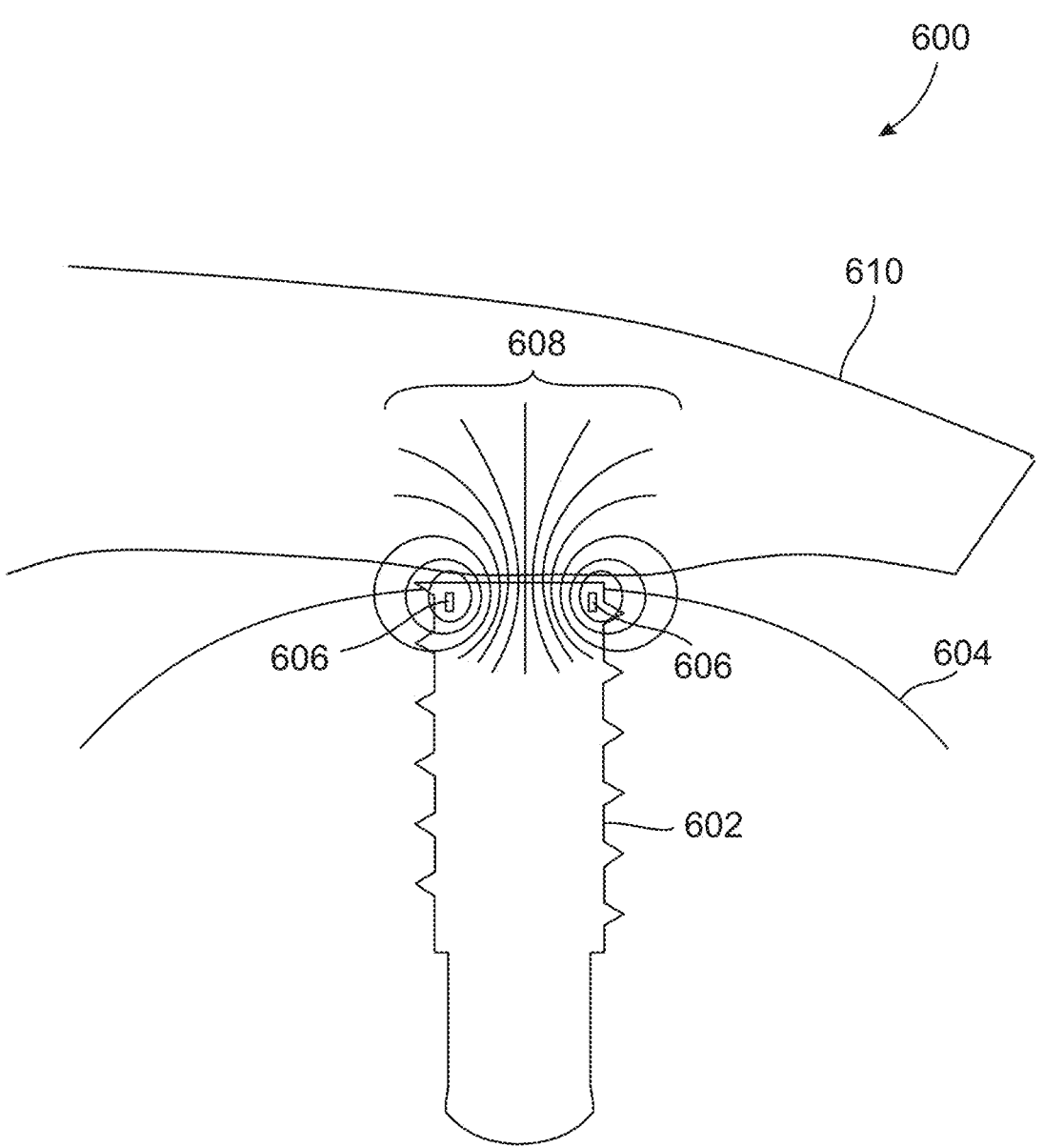
Figure 7:
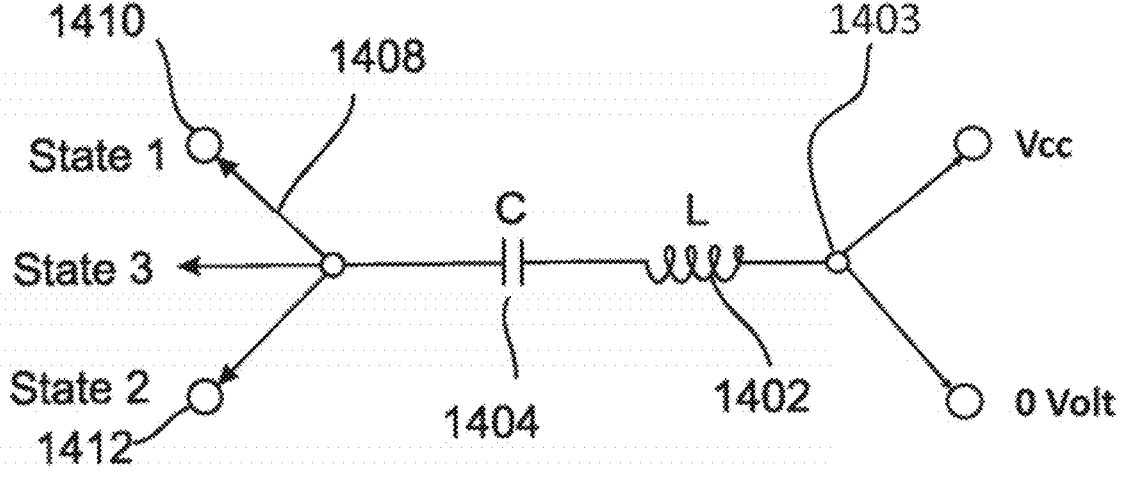
Figure 8:
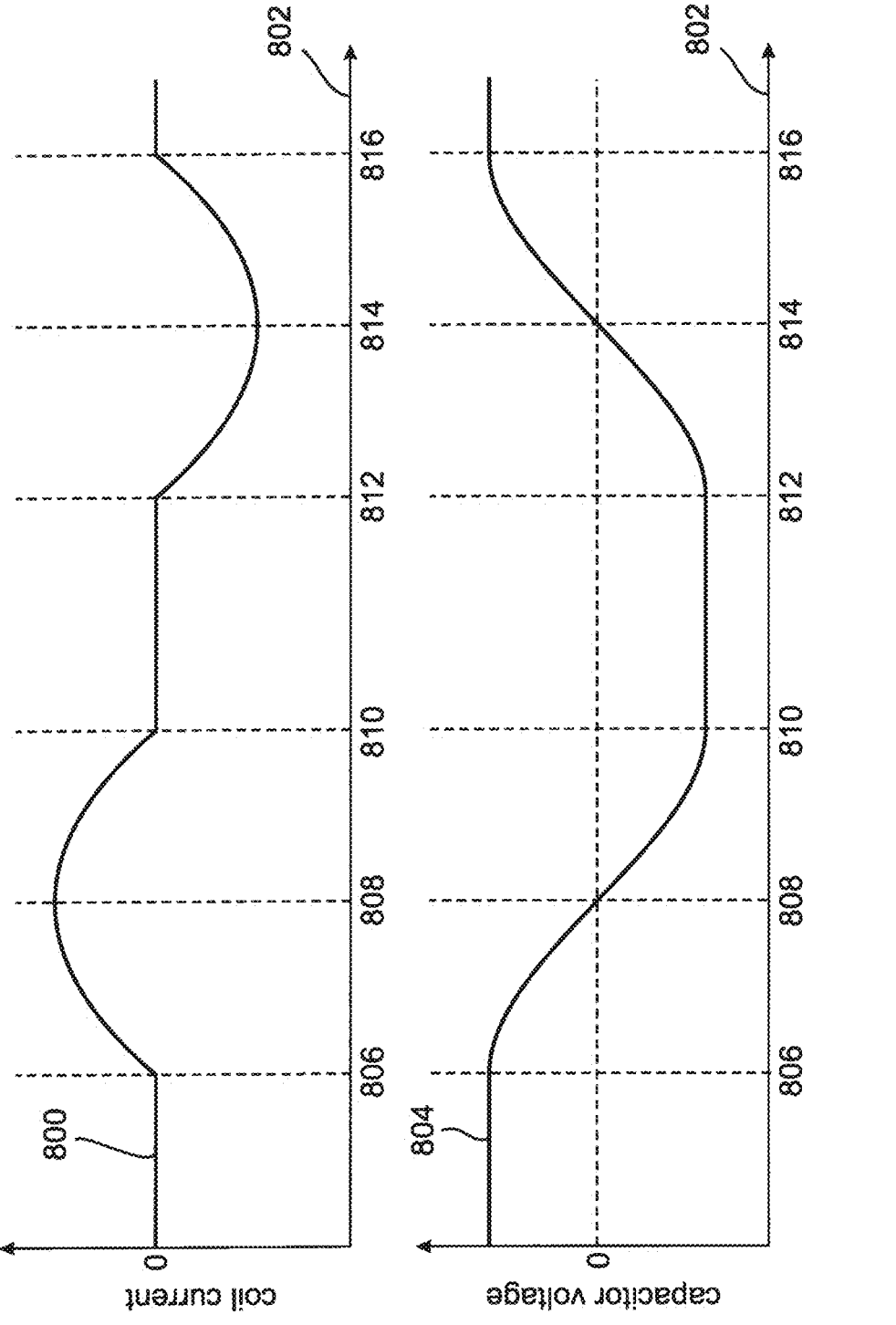
Figure 9:
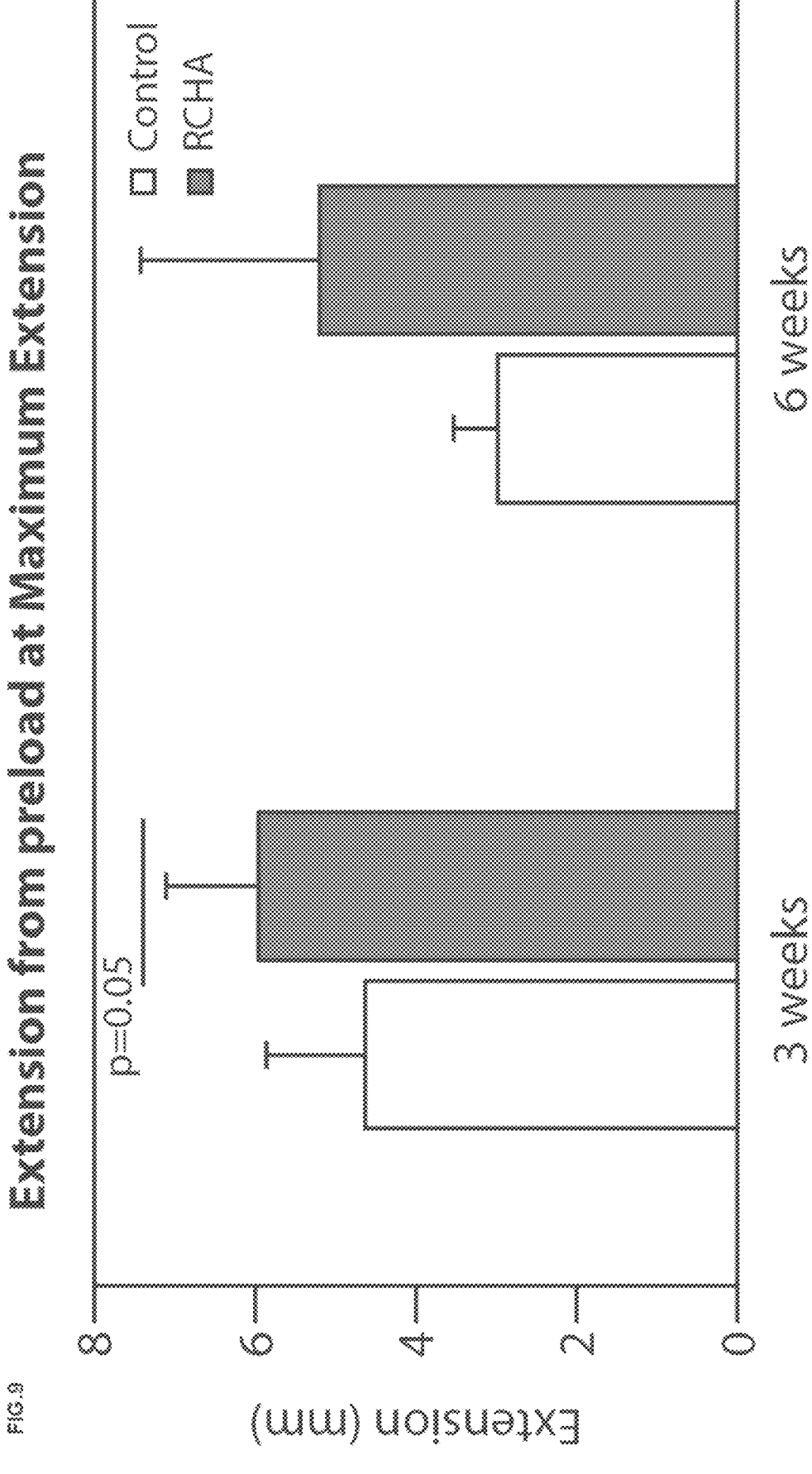
Figure 10:
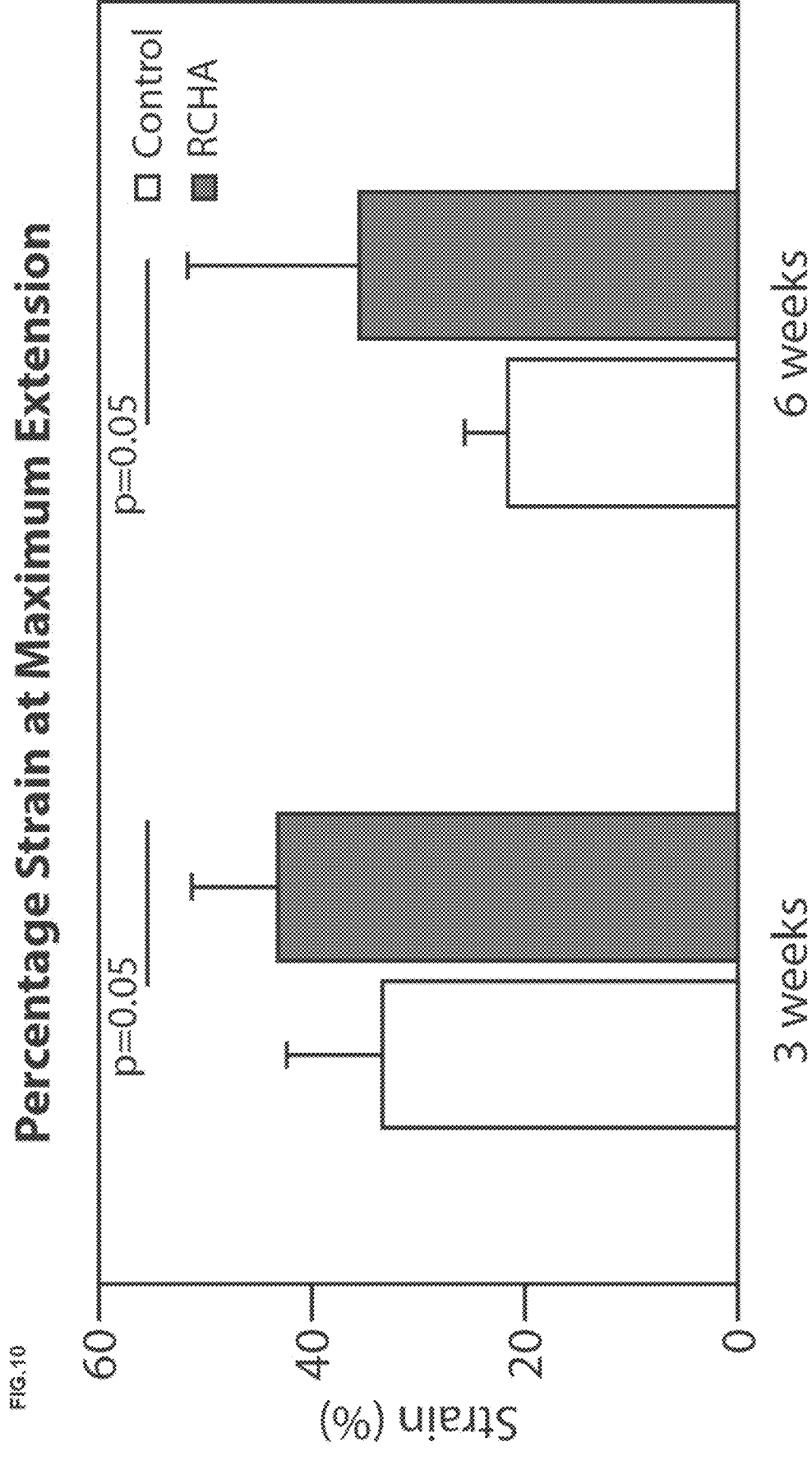
Figure 11:
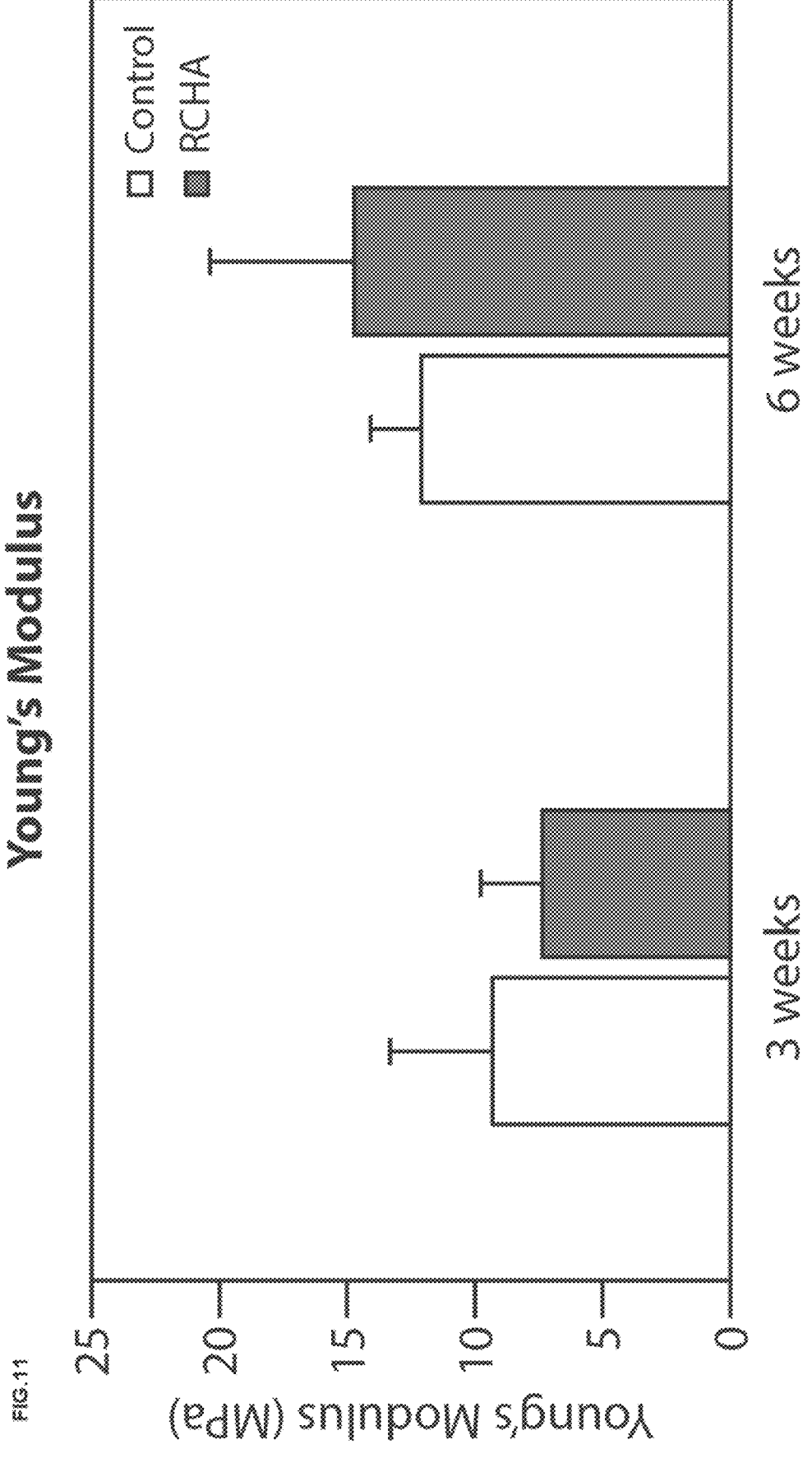
Figure 12:
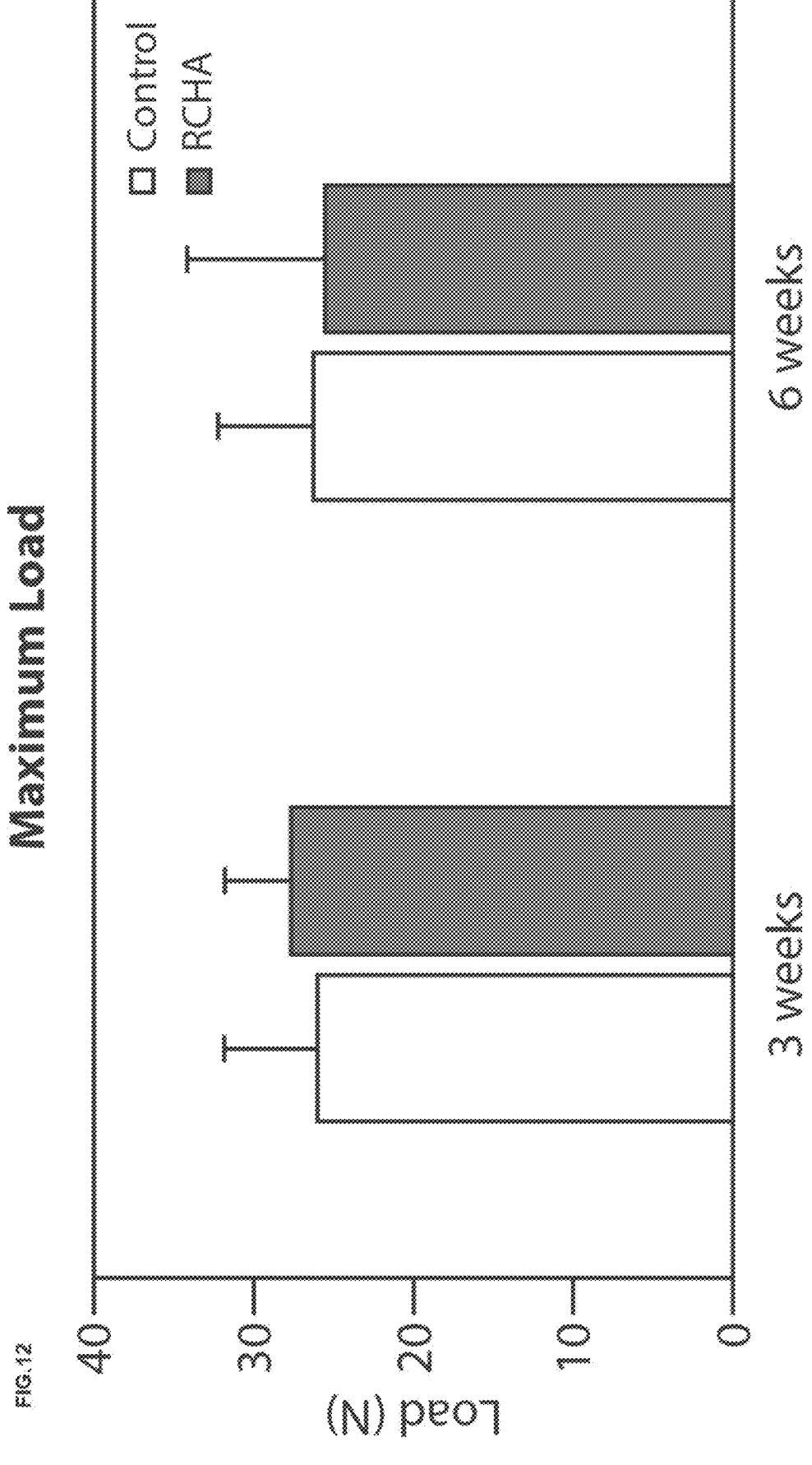
Figure 13:
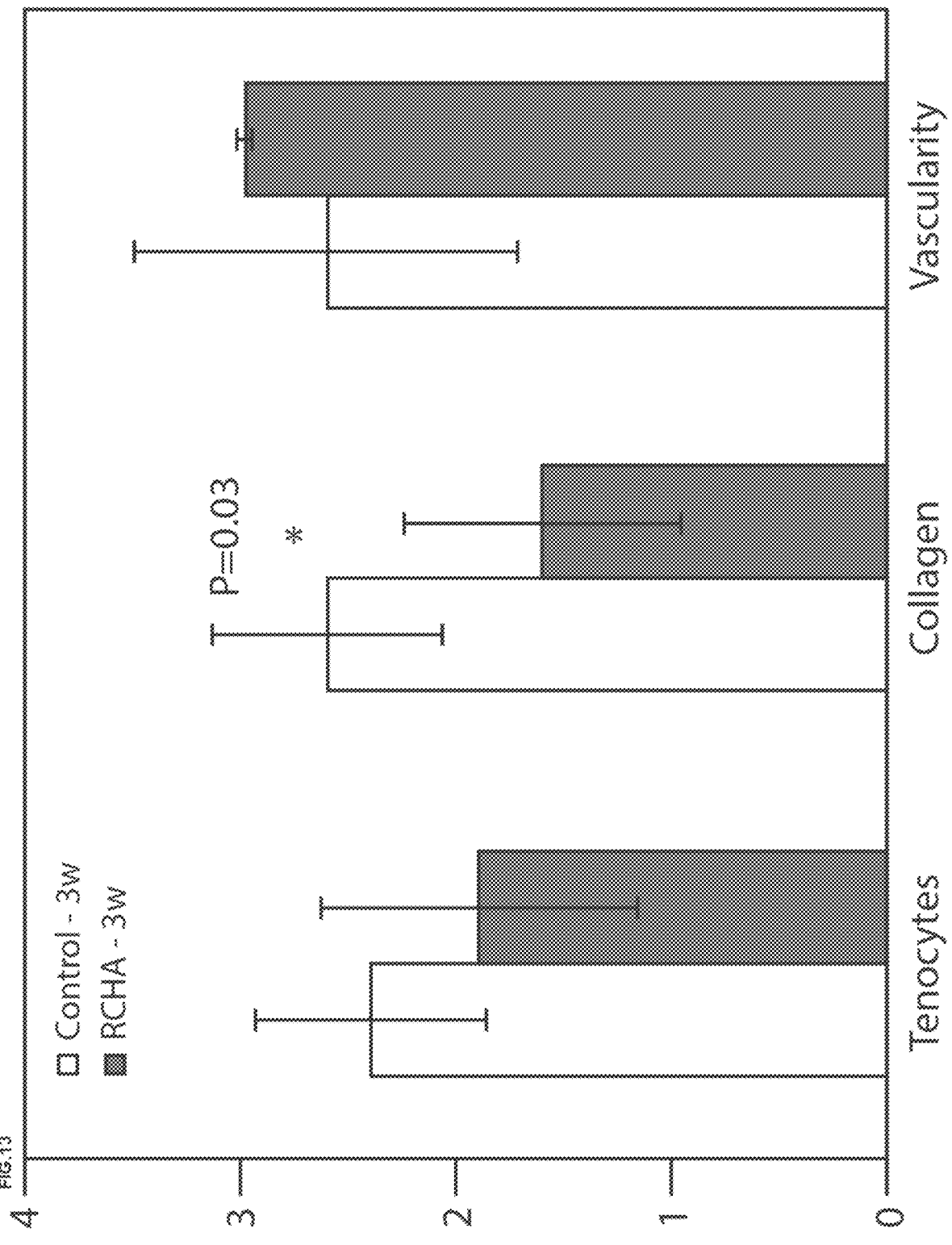
Figure 14:
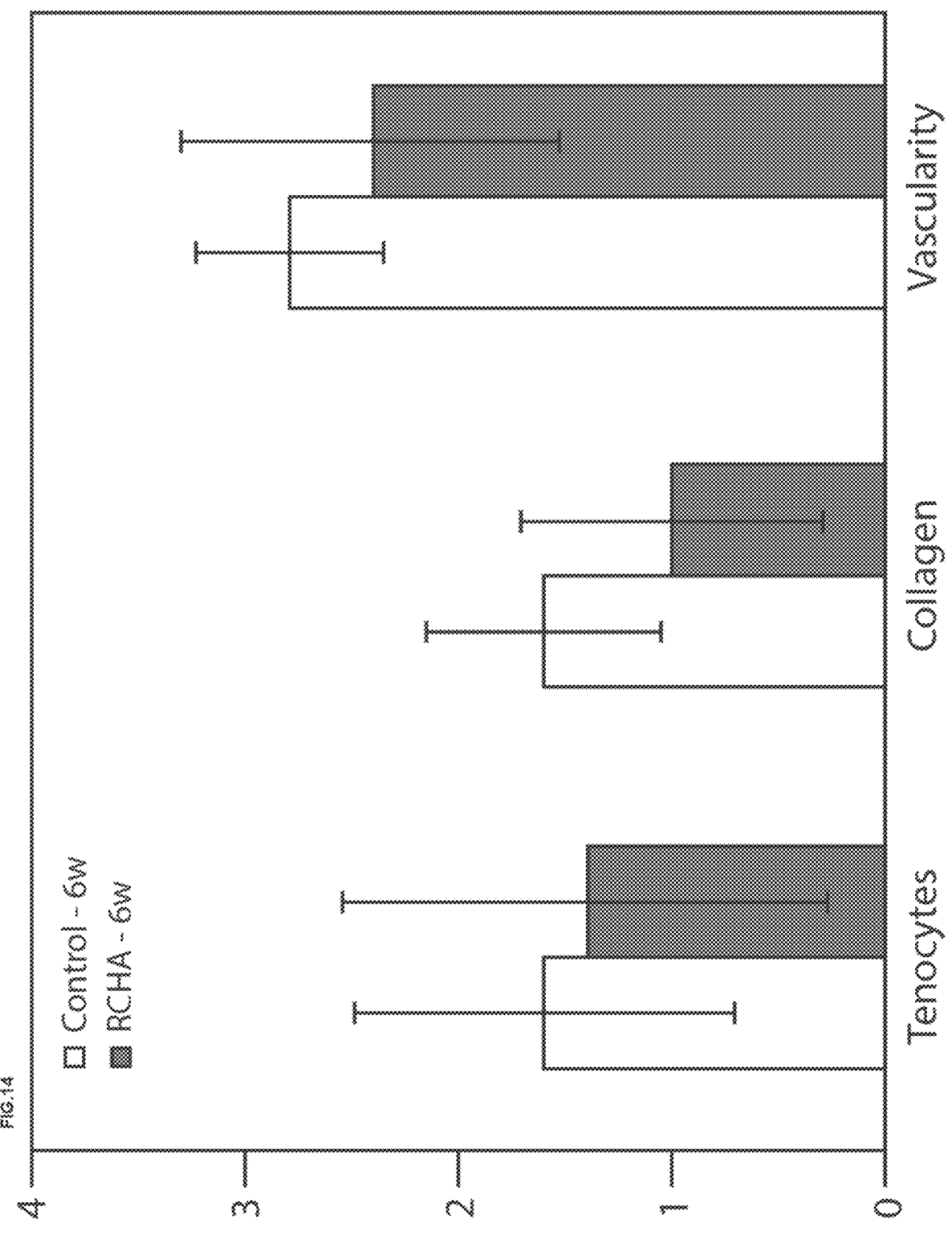
Figure 15:
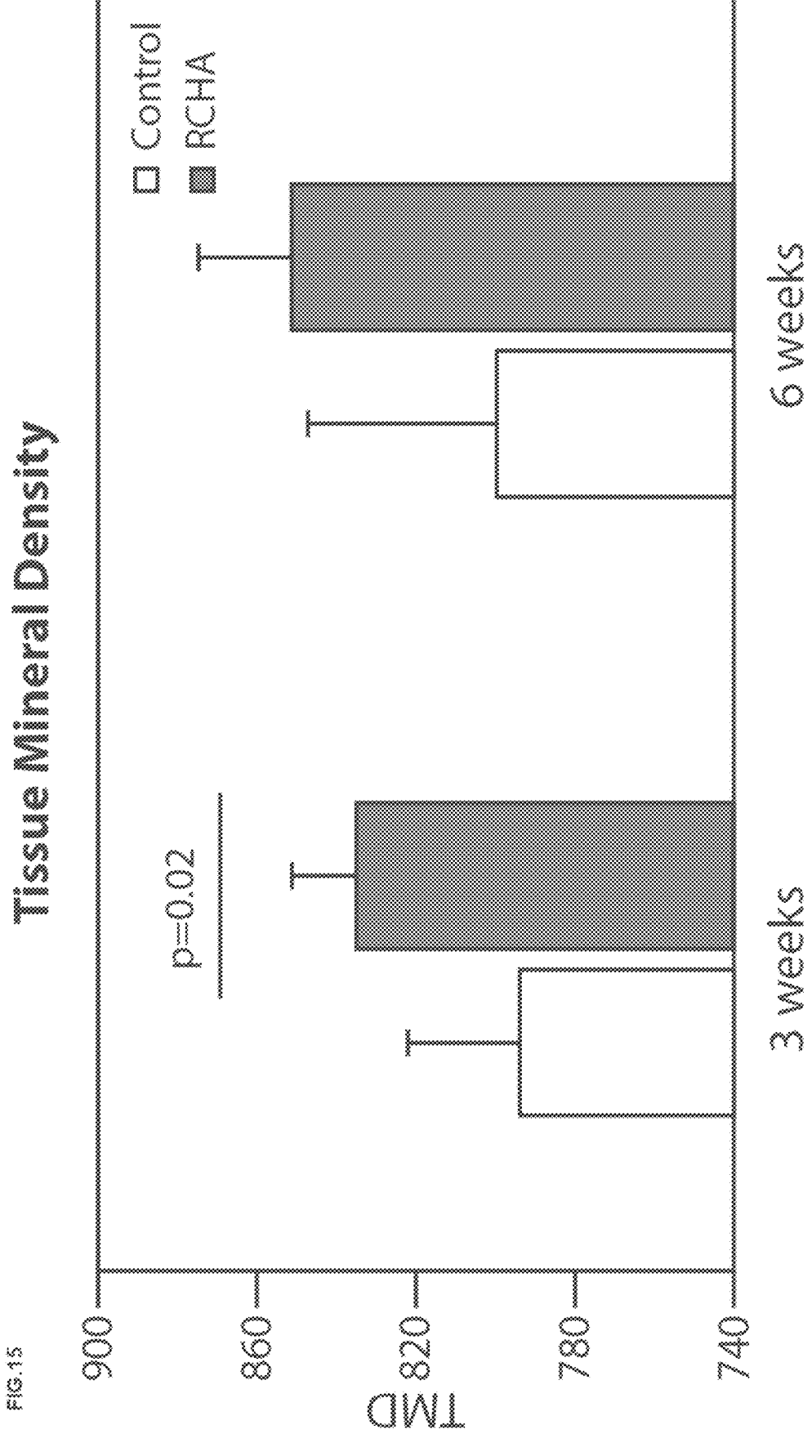
Figure 16:
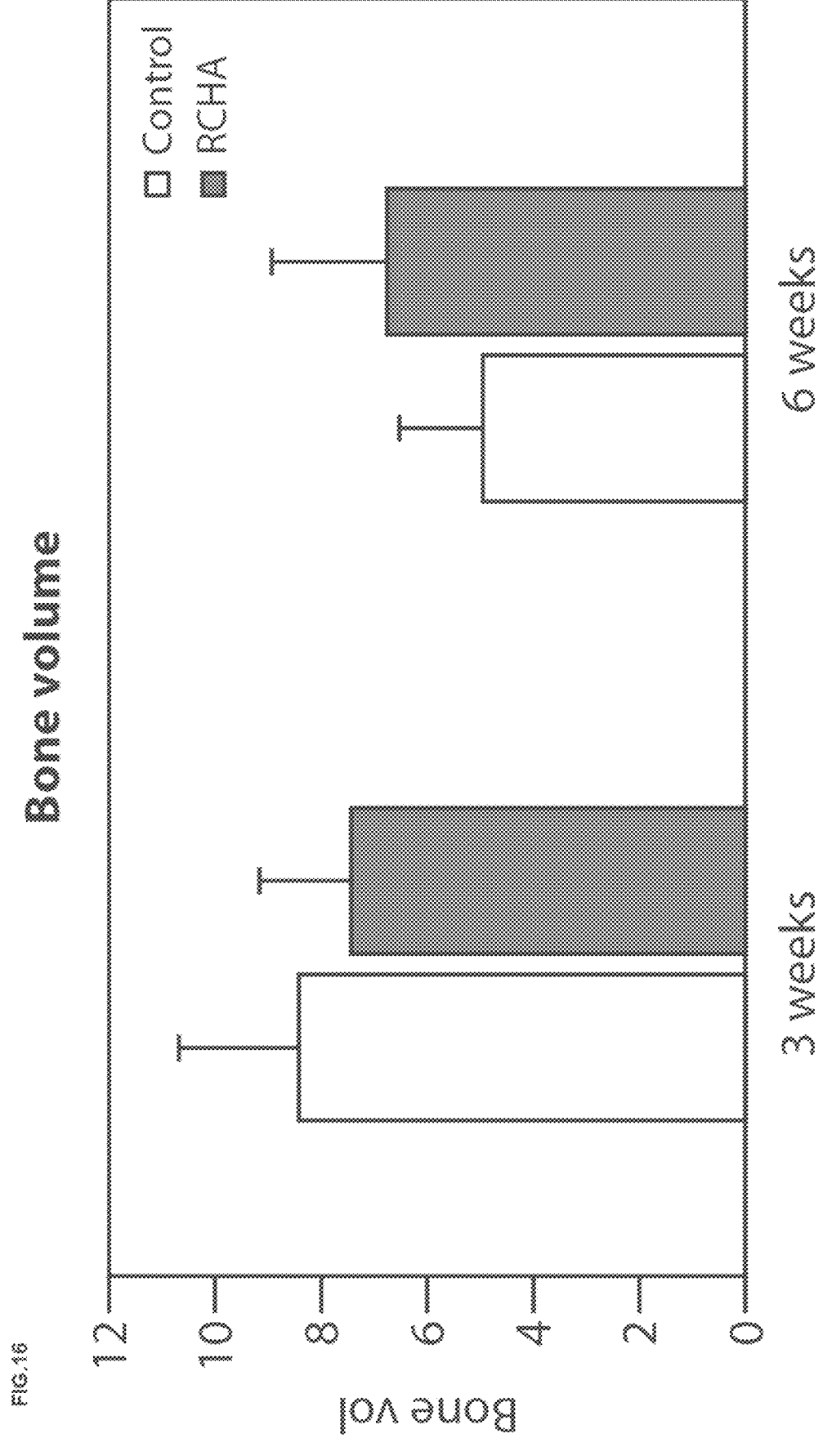
Figure 17:
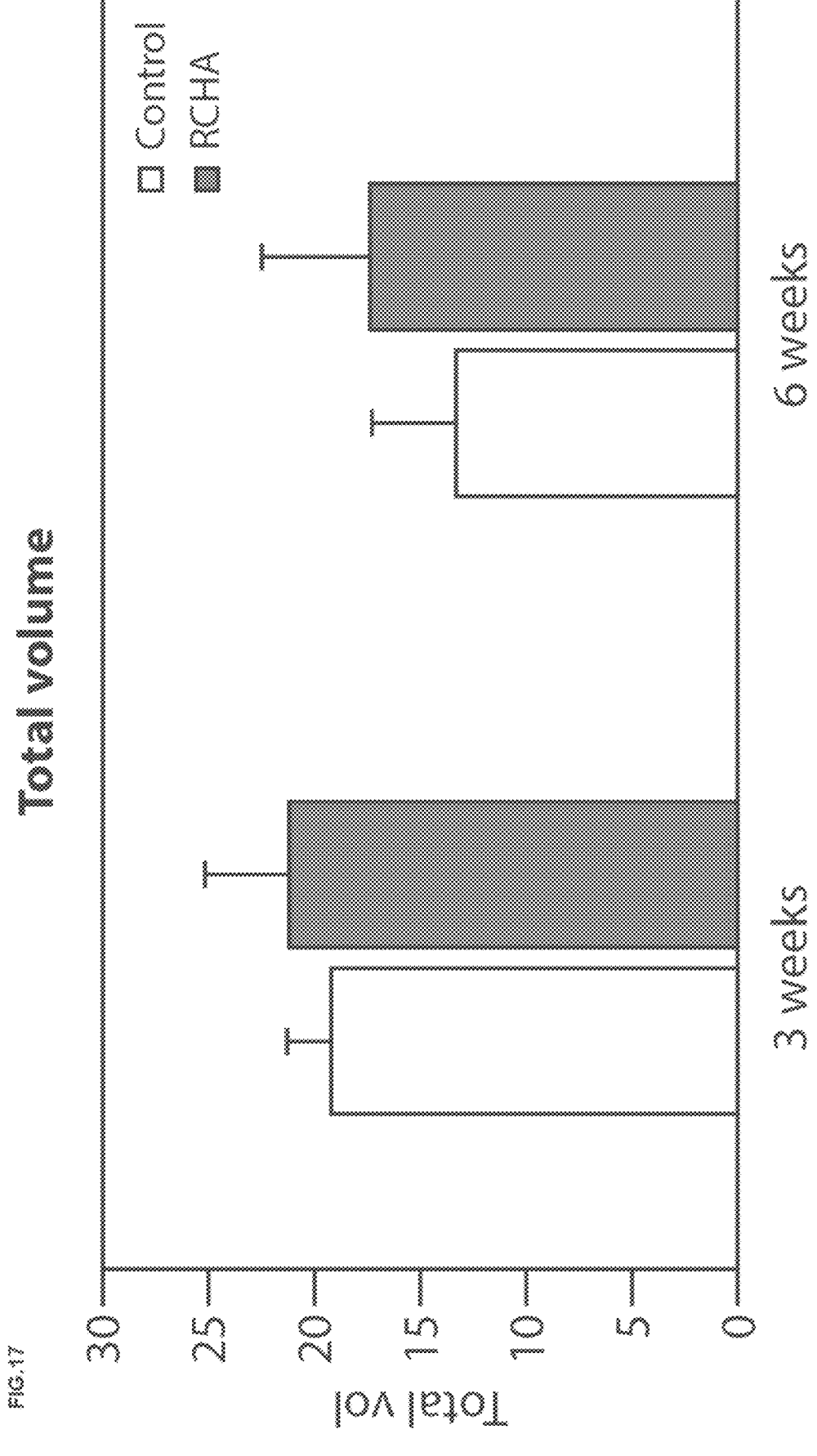
Figure 18:
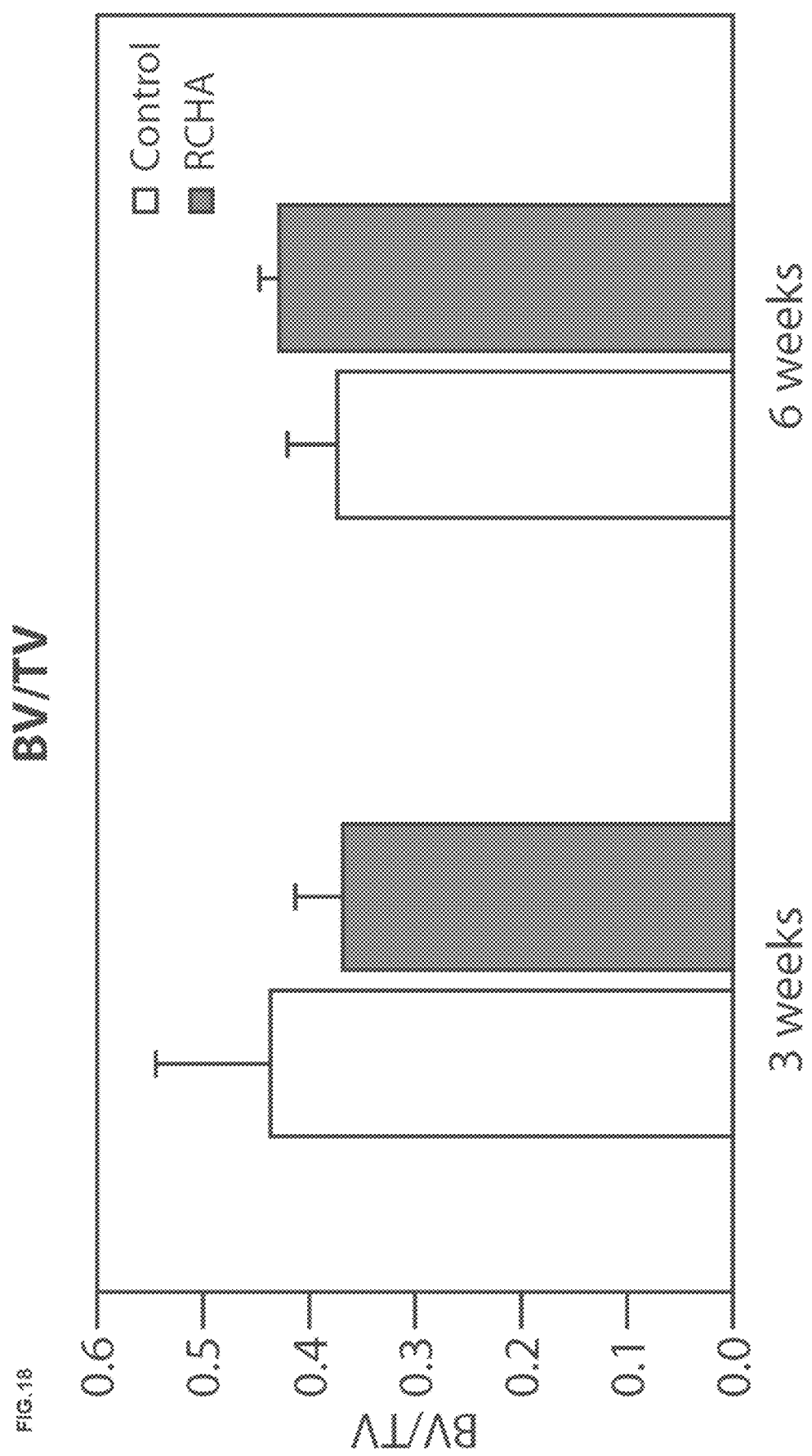

FIGS. 3A, 3B, 3C and 3D schematically shows a perspective view, and side and top cross-sectional views, of a suture anchor containing an EMF generator, which could be used in the method of FIG. 2, according to an exemplary embodiment of the invention;

FIG. 3E schematically shows a driver for driving the suture anchor of FIGS. 3A-3D into a bone, according to an exemplary embodiment of the invention;

FIG. 4A is a cutaway view of an alternative suture anchor containing an EMF generator, showing the coil, electronics module and power source of the EMF generator sealed inside, similar to the anchor shown in FIGS. 3A-3D, according to an exemplary embodiment of the invention;

FIG. 4B schematically shows various designs of suture anchors that could be incorporated with an EMF generator, according to an exemplary embodiment of the invention;

FIG. 4C schematically shows cutaway views of a suture anchor with a different design than those shown in FIGS. 3A-3D and 4A, which does not need a specialized driver coupled to each anchor, according to an exemplary embodiment of the invention;

FIG. 4D schematically shows a suture with a coil inside, according to an exemplary embodiment of the invention;

FIG. 5 schematically shows the suture anchor of FIGS. 3A-3D, embedded in a bone with a tendon sutured to it, according to an exemplary embodiment of the invention;

FIG. 6 schematically shows a side view of the outline of the suture anchor of FIGS. 3A-3D, a side cross-sectional view of the coil in the suture anchor, and parts of some magnetic field lines generated, by current in the coil, in a tendon sutured to the anchor, according to an exemplary embodiment of the invention;

FIG. 7 schematically shows a circuit diagram for part of a resonant energy-saving circuit in the electronics module of the EMF generator of the suture anchors shown in FIGS. 3A-3D and FIGS. 4A-D, according to an exemplary embodiment of the invention;

FIG. 8 schematically shows current in the coil and voltage across the capacitor as a function of time, for the resonant energy-saving circuit of FIG. 7 when it is producing pulsed electromagnetic fields, according to an embodiment of the invention; and FIGS. 9, 10, 11, 12, 13, 14, 15, 16, 17 and 18 show bar charts comparing various measures of recovery from rotator cuff injuries in a rat model, for injuries that were treated by surgery alone, and for injuries that were treated by surgery plus pulsed EMF generated by an EMF generator designed for a dental implant, similar to that described in U.S. Pat. No. 10,376,708, implanted into the body of the rat near the repair seam in the injured rotator cuff, according to an exemplary embodiment of the invention.

DESCRIPTION OF SPECIFIC EMBODIMENTS OF THE INVENTION

The present invention, in some embodiments thereof, relates to a system to promote faster and/or more complete orthopedic healing and, more particularly, but not exclusively, to a system to speed tendon to bone healing especially of a rotator cuff.

An aspect of some embodiments of the invention concerns an anchor for surgically reattaching injured soft tissue to a bone, where the anchor includes an electromagnetic field (EMF) generator that generates a therapeutic EMF in the soft tissue, to promote healing, for a treatment period after the surgery is complete. The anchor comprises a coil that generates the electromagnetic field when current flows through it, an electronics module/controller that controls the amount and timing of the current flowing through the coil, and an electric power supply that provides power to the coil and the electronics module. The anchor also comprises an affixing portion for affixing the anchor to the bone.

Optionally, the soft tissue is a torn tendon. Alternatively, the soft tissue comprises cartilage, a muscle, a ligament, or skin. The anchor designs that have been developed by the inventor are especially suitable for a torn rotator cuff tendon, and the soft tissue will often be referred to herein as a torn tendon, but it should be understood that whenever a torn tendon is mentioned, the statement can also apply to any other soft tissue that is connected to bone.

Optionally, the affixing portion of the anchor has screw threads for screwing the anchor into the bone. Alternatively the anchor is affixed by insertion or punching into the bone, and/or by adhering to the bone by adhesive.

Optionally, the anchor is a suture anchor, with more or more eyelets for attaching a suture, which are used for suturing the torn tendon, or other soft tissue, to the anchor.

Optionally, the anchor has a driver fitting into which, and/or around which, a driver is inserted, which is used to drive the anchor into the bone, for example by screwing the anchor into the bone. Optionally, the coil is located near a proximal end of the anchor, near the torn tendon when it is reattached, and optionally, when the driver is inserted into the anchor, the driver extends through the center of the coil.

As used herein, the axis of the anchor is the direction along which the anchor penetrates into the bone. The axis has a distal direction, the direction toward the bone when the anchor is driven into the bone, and a proximal direction, the direction away from the bone. The proximal end of the anchor, as used herein, means the point of the anchor that is furthest in the proximal direction. Optionally, most of the conductor volume of the coil is located within 0.5 mm or within 1 mm or within 2 mm or within 3 mm or within 5 mm, in the axial direction, of the proximal end of the anchor. Optionally, most of the conductor volume of the coil is located within $\frac{1}{10}$ of the anchor length, or within $\frac{1}{5}$ of the anchor length, or within $\frac{2}{5}$ of the anchor length, of the proximal end of the anchor.

Optionally the orientation of the coil, defined herein as the direction of the magnetic moment of the coil when it has a dc current running through it, is within 5 degrees, or within 10 degrees, or within 20 degrees, or within 30 degrees, or within 45 degrees of the direction of the axis of the anchor.

Optionally, a proximal part of the anchor is substantially a circular cylinder, aside from any threads for screwing it into the bone, and the outer limits of the coil fill up a large fraction of the area of the circular cross-section of the proximal part of the anchor, for example at least 90% of the area, or at least 80%, or at least 70%, or at least 50%. Optionally, the coil's greatest diameter is greater than 7 mm, or between 5 and 7 mm, or between 3 and 5 mm, or less than 3 mm. Optionally the coil is substantially circular, which potentially maximizes its magnetic moment for a given area that it takes up. Optionally, the proximal part of the anchor has a diameter greater than 7 mm, or between 5 and 7 mm, or between 3 and 5 mm, or less than 3 mm. It is potentially advantageous if the anchors have diameters close to, or identical to, existing suture anchors, so that surgeons can perform their surgery using the anchors in the way they are used to, and selecting the anchor size to use according the same criteria they have used before, depending on the surgical procedure that is being performed, and the size of the bone and the soft tis sue.

Optionally, an effective length of the coil, in a direction along its magnetic moment, is less than an effective diameter of the coil, perpendicular to its magnetic moment. The effective length is, for example, twice the standard deviation of the distribution of conductor volume of the coil, in the direction of the magnetic moment of the coil. The effective diameter is, for example, the maximum extent of the conductor volume of the coil, in a direction perpendicular to the direction of the magnetic moment of the coil. For example, if the coil is a uniform circular cylindrical coil, then the effective length is the length of the coil divided by $\sqrt{3}$, and the effective diameter is the outer diameter of the coil. Alternatively, the effective length is less than 5% of the effective diameter, or less than 10%, or less than 15%, or less than 25%, or less than 35%, of the effective diameter, or less than 50% of the effective diameter, or less than 75% of the effective diameter, or less than 1.5 times the effective diameter, or less than 2.5 times the effective diameter.

Having the coil located near the proximal end of the anchor, and/or oriented close to the direction of the axis of the anchor, and/or nearly circular, shorter than its radius, or at least not too much longer than its diameter, and/or extending out to a large fraction of the diameter of the proximal part of the anchor, may result in the magnetic field generated by the coil being relatively high in intensity, over a relatively large volume of the tendon, especially in the vicinity of the suture, for a given electric power consumed by the coil. For example, the magnetic field is at least 2 mT, or at least 1 mT, or at least 0.5 mT, or at least 0.3 mT, or at least 0.2 mT, or at least 0.1 mT, at at least one location more than 1 mm, or more than 2 mm, or more than 3 mm from all of the coil in the proximal direction. Optionally, the magnetic field is pulsed, or at least alternating, so the coil also produces an electric field in the tendon in the vicinity of the suture, for example at least 0.5 V/m, or at least 0.3 V/m, or at least 0.2 V/m, or at least 0.1 V/m, or at least 0.05 V/m, or at least 0.03 V/m, or at least 0.02 V/m, or at least 0.01 V/m or at least 0.005 V/m, at at least one location more than 1 mm, or more than 2 mm, or more than 3 mm from all of the coil in the proximal direction. Such a coil design may improve the therapeutic effectiveness of the electromagnetic fields, to encourage healing of the tendon, and/or to improve elasticity and/or collagen expression in the tendon, for a given stored energy in the power source.

Alternatively, instead of a pulsed magnetic field produced by a coil, which induces an electric field, a DC magnetic field is produced by DC current in the coil, or a steady AC magnetic field is produced by a sinusoidal AC current in the coil, or an electric field is produced in the tendon using electrically charged plates, or an antenna other than a coil is used to produce electromagnetic fields in the tendon. But in some embodiments, a pulsed magnetic field is produced by pulsed current in the coil, which induces an electric field in the tendon, as described above, and this configuration is believed to be therapeutically useful.

Optionally, the coil is an air core coil. Alternatively, the coil has a core of high permeability material, such as ferrite. Optionally, the ferrite core is hollow in the middle. For a coil that has a length much less than its diameter, the presence of a ferrite core may hardly affect the field produced by the coil for a given current. But for a coil that has a length comparable to its diameter, having a ferrite core may significantly increase the field produced outside the core.

Optionally, the anchor has eyelets for attaching one or more sutures, with at least one eyelet located distal to the coil, or passing through the coil. Such a configuration has the potential advantage that it may allow the coil to be as close as possible to the tendon, which is generally located close to the proximal end of the anchor. Optionally, the electronics module and the power source are located distal to one or more or all eyelets.

Optionally, the electromagnetic field generator generates pulses of current through the coil that are longer than 10 ms, or between 5 and 10 ms, or between 2 and 1 ms, or between 500 μs and 1 ms, or between 200 and 500 μs, or between 100 and 200 μs, or between 50 and 100 μs, or between 20 and 50 μs, or between 10 and 20 μs, or shorter than 10 μs. Optionally, each pulse is substantially an integer number of sine wave cycles, or a half-integer number of sine wave cycles, for example a half a cycle, or 1 cycle, or 1.5 cycles, or 2 cycles. Having each pulse an integer or half-integer number of cycles potentially allows most of the electromagnetic field energy of the coil to be stored in a capacitor for a relatively long time between pulses, with very little energy dissipated. The frequency of the sine wave in this case is the LC resonance frequency of the capacitance of the capacitor and the inductance of the coil. In the tests with rats done by the inventors, described in FIGS. 9-18, the resonance frequency was 20 kHz, and each pulse was one cycle long, which was 50 μs. This pulse length was found to be effective in promoting healing by a variety of measures. Optionally, the pulse repetition rate is less than 1 Hz, or between 1 and 2 Hz, or between 2 and 5 Hz, or between 5 and 10 Hz, or between 10 and 20 Hz, or between 20 and 50 Hz, or between 50 and 100 Hz, or more than 100 Hz. Optionally, at least 50% of the energy of the electromagnetic field in each pulse, or at least 80%, or at least 90%, or at least 95%, or at least 99%, is stored in the capacitor between pulses, and returned to the coil for the next pulse. Re-using the same field energy for many pulses, with very little loss from one pulse to the next, has the potential advantage that for a given field intensity and duty cycle, the power source can last longer.

Optionally, the electric power source comprises one or more batteries. Optionally, the batteries are not rechargeable. Alternatively, the batteries are rechargeable. Optionally, the power source comprises a charged capacitor. Optionally, if the power source is rechargeable, the electronics module includes a circuit for inductively recharging the power source from outside the body. If the power source cannot be recharged from outside the body, then the energy initially stored in the power source is enough to provide a pulsed electromagnetic field for a duration of treatment of the tendon.

An aspect of an embodiment of the invention concerns a method of treating a patient with an injury to soft tissue that is attached to bone, such as a torn tendon, using electromagnetic fields generated by an EMF generator associated with a suture anchor that is used to suture the soft tissue to the bone. Optionally, the EMF generator is well encased in the suture anchor, which has the potential advantage that it can remain indefinitely in the body, without concern that dangerous materials in the EMF generator might leak out into the body. The EMF generator is designed to generate significant therapeutic fields in a region close to the proximal end of the anchor, where the torn end of the tendon will be located after suturing. The EMF generator continues to generate the fields for a treatment period after suturing the tendon to the anchor, for example less than 1 day, or between 1 day and 1 week, or between 1 week and 1 month, or between 1 and 3 months, or between 3 months and 1 year, or more than 1 year. Optionally, the EMF generator is left in the anchor, and in the body, indefinitely, even after the treatment period, for example for at least 1 year after the treatment period, or for the remaining lifetime of the patient. Optionally, the anchor is configured to keep the components of the EMF generator safely encased and sealed inside the anchor for an indefinite time, for example for at least an expected lifetime of the patient, without any leaking.

Optionally, the anchor is threaded, and is screwed into the bone by using a driving tool that is inserted into a driver fitting of the anchor. Alternatively, an interference fit is used, such as in a Rawl bolt. Optionally, a self-punching mechanism is used.

Optionally, the electromagnetic fields are pulsed, with a duty cycle of less than 10, or between 10 and 100, or between 100 and 1000, or between 1000 and 10,000, or more than 10,000.

In addition to producing therapeutic EMF in the tendon, optionally the anchor releases drugs that may be therapeutically useful, in conjunction with the EMF. For example, the anchor may release, possibly slowly over time, steroids, anti-inflammatory drugs, bone enhancement drugs, ligament healing factors, etc.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present disclosure may take the form of a computer program product embodied in one or more computer readable medium(s) having computer readable program code embodied thereon.

Implementation of the method and/or system of some embodiments of the disclosure can involve performing and/or completing selected tasks manually, automatically, or a combination thereof. Moreover, according to actual instrumentation and equipment of some embodiments of methods, systems, and/or computer program products of the present disclosure, several selected tasks could be implemented by hardware, by software or by firmware and/or by a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computer using any suitable operating system. In an exemplary embodiment, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1A:
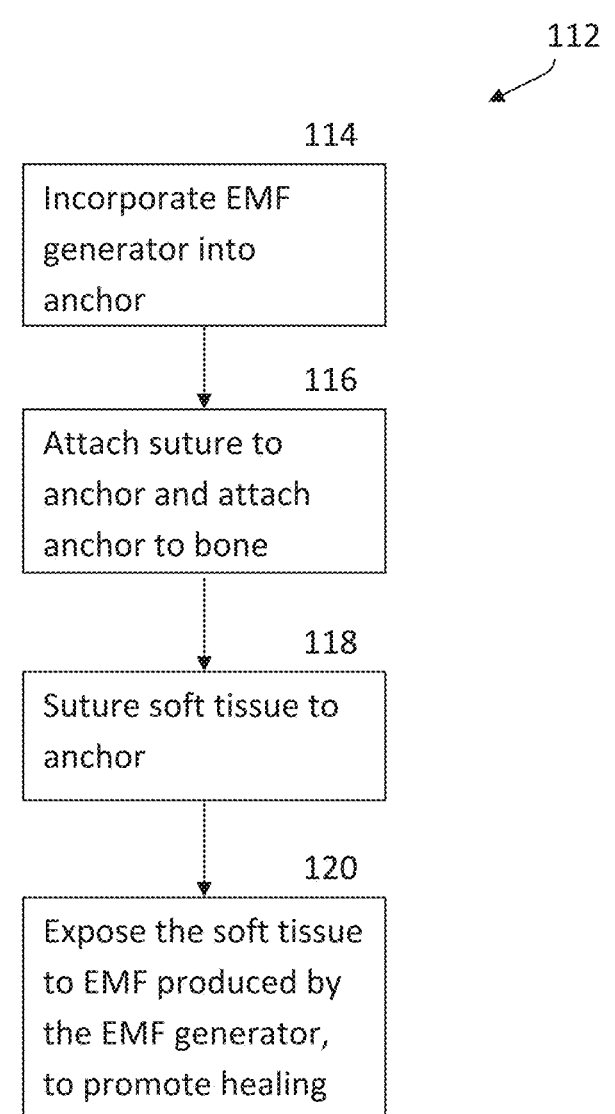
FIG. 1A is a flowchart for a general method of assembling an anchor with an EMF generator and using it to treat injured soft tissue, according to an exemplary embodiment of the invention.

Referring now to the drawings, FIG. 1A illustrates a flowchart 112 for a general method of assembling an using a suture anchor that incorporates an EMF generator, for treating injured soft tissue using surgical attachment of the soft tissue to bone, and using the EMF generator to generate therapeutic EMF to promote healing of the injury following the surgery. At 114, the EMF generator is incorporated into the anchor, for example by encasing it inside the anchor. At 116, a suture, or more than one suture, is attached to the anchor, and the anchor is then attached to the bone. At 118, the suture is used to suture the injured soft tissue to the anchor. At 120, the EMF generator generates EMF in the soft tissue, for example pulsed EMF of an amplitude, pulse length and pulse repetition rate suitable for pulsed EMF (PEMF) therapy. This is done for a period of time, for example one day, or one week, or one month, or three months, or 6 months, or a year, or a greater or shorter or intermediate period, to promote healing the soft tissue after the surgery.

Figure 1B:
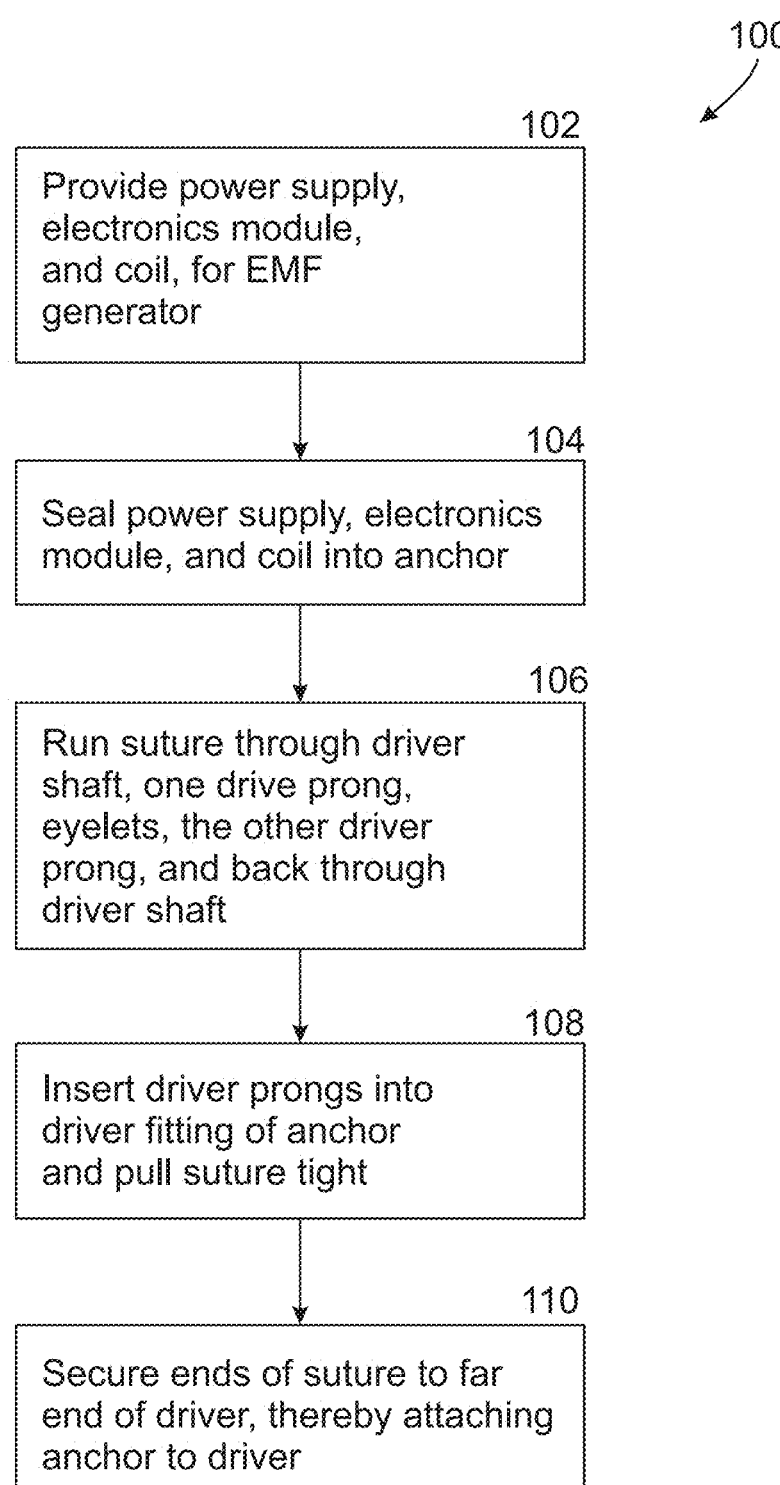
FIG. 1B is a flowchart for a method of assembling a particular exemplary design of suture anchor containing an EMF generator for generating therapeutic EMF, according to an exemplary embodiment of the invention.

FIG. 1B shows a flowchart 100 for a method of assembling a suture anchor with an electromagnetic field (EMF) generator inside it, for a particular design of suture anchor such as those shown in FIGS. 3A-3D and FIG. 4A. At 102, an electric power supply, an electronics module, and a coil are provided, for the EMF generator. The electronics module includes a controller for controlling the current that passes through the coil as a function of time, which in turn affects the magnetic fields and electric fields produced by the coil in the vicinity of the anchor. The controller includes a signal generator which generates a signal that controls the current flow as a function of time. Optionally, the EMF generator produces short pulses of electric and magnetic fields, caused by short pulses of current through the coil, with periods much longer than the pulse length during which little or no current passes through the coil, and little or no electromagnetic field is produced. Optionally, the electronics module includes a resonant energy-saving circuit that stores most of the field energy or almost all of the field energy of each pulse in a capacitor between pulses, with very little energy dissipated between pulses, and uses most or almost all of the stored energy to generate the next pulse. The power supply provides electric power to the electronics module and to the coil, including the power needed initially to produce pulses before the capacitor is fully charged, and the power needed to replace any of the pulse energy that is dissipated, for example by ohmic losses in the coil.

At 104, the power supply, electronics module and coil are encased inside the anchor. The casing is made, for example, of titanium, zirconia, PEEK, and/or other bio-compatible material with high mechanical strength and/or chemical resistance. Optionally, the casing is permanently sealed, with a design that is not expected to leak for the life expectancy of the patient. Such casing can isolate any dangerous materials, for example material leaking from batteries, such as lithium batteries used for the power source, from the body of the subject. Optionally, the casing is big enough in volume and strong enough so that it can contain gases leaking from batteries, without deforming enough to adversely affect the function of the anchor, and without weakening enough to break and allow the gases to leak out. Alternatively or additionally, components of the device are made of safe materials. For example, rather than a lithium battery power source, the device may include a supercapacitor and/or an enzyme battery. In some embodiments, the device may be activated and/or adjusted wirelessly (for example using a reed switch). Activation and/or adjustments may be made for example before implantation, during implantation and/or during use.

Optionally, the power source stores enough energy to power the EMF generator for as long as the EMF therapy is supposed to continue. Alternatively, in cases where a power source does not store enough power for the entire therapy, the power source may be recharged wirelessly. For example, the coil that is used for producing the therapeutic field may be used as an antenna for inductive charging.

Optionally, the coil is first wound and embedded in epoxy or another insulating material, using any known method of winding a coil, and the wound coil is then embedded in the anchor, for example by using injection molding or 3-D printing, if the body of the anchor is made of plastic that can be shaped by those methods. Alternatively, depending on the material of the anchor, a space that just fits the wound coil is machined out the anchor, and coil is inserted in it. When the coil is imbedded in the body of the anchor, its electric leads are not imbedded in the body of the anchor, but are left free, to be connected to the electronics module that drives the coil. Alternatively, the previously wound coil is not embedded in the anchor during injection molding, but is attached to the body of the anchor, after the body is made, for example by an adhesive. Alternatively, the coil is not wound separately, but is wound in place on the anchor, for example in a groove that encircles the anchor near its proximal end, and the groove is then filled in, for example with epoxy, to protect the coil. In this case also, the leads of the coil are passed into the interior of the anchor, where they can be connected to the electronics module.

At 106, one or more sutures are attached to the anchor. Optionally, the sutures are attached to the anchor through a driver that will be used to drive the anchor into a bone. The driver, for example, has a handle, a driver shaft, and two prongs that couple in two slots in the proximal surface of the anchor, as shown in FIG. 3E, below. The suture is run down through the driver shaft which is hollow, through one of the prongs, which are also hollow, and into one of the driver slots in the anchor. The suture is then passed through an eyelet, an internal opening in the anchor that connects the two slots. Optionally, if the anchor is to be used with more than one suture, there is more than one eyelet, and each suture is passed through a different eyelet. The suture then passes out of the second slot, into the second prong of the driver, and back up the driver shaft.

At 108, the driver prongs are inserted in the driver slots of the anchor, and the one or more sutures are pulled tight. At 110, the ends of the one or more sutures are tied to the far end of the driver, for example to the driver handle. This attaches the driver to the anchor, and the anchor is sold this way, attached to the driver.

Elements 106, 108 and 110 of flowchart 100 are similar to the steps done when assembling conventional suture anchors, which do not have EMF generators encased in them. However, there may be some differences due to the presence of the EMF generator. For example, if the electronics module and the power source fill up much of the cross-sectional area of the anchor, then optionally the electronics module and power source are located in a more distal part of the anchor, and the slots and eyelets are located in a more proximal part of the anchor, with no need for spaces between and around the power source and electronics module for the sutures to run through. Optionally, the coil is also in a more distal part of the anchor than the driver slots and eyelets. However, it is potentially advantageous for the coil to be located near the proximal end of the anchor, near the tendon where the electromagnetic fields produced by the coil are expected to have a therapeutic effect, so that the electromagnetic fields can be sufficiently intense at the suture location of the tendon to have the desired therapeutic effect, while keeping the stored energy requirements for the power source relatively low. In this case, the coil optionally surrounds the proximal portion of the slots, and the suture passes through the center of the coil when it goes into one of the slots, and passes back through the center of the coil when it goes back up through the other slot.

FIG. 2 shows a flowchart 200 for a method of using a suture anchor, assembled by the method of flowchart 100, to suture a torn tendon to a bone, and then to expose the tendon to therapeutic EMF while it is healing. At 202, the anchor is driven into the bone with the driver, optionally completely, until the top surface of the anchor is level with the surface of the bone, or even slightly below the level of the bone. The bone is the bone at which the tendon was torn. For example, in the case of a rotator cuff injury, the bone is the humerus. In the example shown in FIGS. 3A-3E, the anchor has screw threads, and the driver is used as a screw driver, to screw the anchor into the bone. Alternatively, the anchor is attached to the bone in some other way at 202, for example by inserting it in a previously made hole in the bone into which it fits snugly, or using an adhesive to hold the anchor in the hole, or using an adhesive to attach the anchor to the surface of the bone, or by using the driver to punch the anchor into the bone. In these cases, the driver might not serve the function of driving the anchor into the bone, but can still serve the function of keeping the suture from slipping out of the anchor, while the anchor is being stored before using it.

At 204, the ends of the suture are released from the driver. At 206, the driver is removed from the anchor and the suture, leaving suture attached to the anchor. At 208, the suture, or the sutures if there is more than one, is used to attach the torn tendon to the anchor, and hence to the bone. At 210, the EMF generator is used to generate EMF, for example pulsed EMF, in a part of the tendon adjacent to the anchor, which is generally the part of the tendon that has been sutured to the anchor. Optionally, the EMF generator is turned on manually, for example by using a switch on the anchor, before closing up the surgical incision. Alternatively, the EMF generator is turned on remotely, from outside the body, for example by using a switch that is activated by radio waves.

The generated EMF has characteristics, such as amplitude of the magnetic and electric fields, pulse time, and repetition time of the pulses, that are expected to promote healing of the tendon, and/or to improve elasticity and/or collagen expression in the tendon. The magnetic field is generated by the current in the coil, according to the Biot-Savart law. The electric field is then generated by the changing magnetic field, according to Faraday's law. Optionally, the frequency of the electromagnetic field is low enough, and the EMF generator is small enough, so that the displacement current is negligible compared to the coil current, and radiative effects can be ignored. In particular, radiative energy losses can be ignored compared to ohmic losses in the coil.

The generation of EMF by the generator continues for a treatment period, after the surgery is complete. For example, the treatment period may be less than 1 day, or between 1 day and 1 week, or between 1 week and 1 month, or between 1 and 3 months, or between 3 months and 1 year, or more than 1 year. Optionally, the power source has enough stored energy to continue to provide power to the EMF generator, to generate EMF at the selected parameters, for the entire course of treatment.

At 212, the EMF generator, sealed inside the anchor, which is attached to the bone, is left inside the body permanently, even after the treatment ends.

FIG. 3A shows an external perspective view of a suture anchor 300, according to an exemplary embodiment of the invention. Threads 302 allow the anchor to be screwed into bone, and to remain affixed to the bone even when the anchor is subject to the forces exerted on it by the suture, when the tendon is sutured to the anchor. Alternatively or additionally, an anchor may include an interference fitting for grasping bone and/or tissue. Driver fittings 304, in the form of slots, are used to couple the anchor to the driver well enough to be able to drive the anchor into the bone. Optionally, there is a hollow space 306 at the distal end of the anchor, for example to facilitate fixation into the bone. Planes B-B and C-C in FIG. 3A show the planes respectively of the cross-sectional views shown in FIGS. 3B and 3C. The proximal and distal directions of anchor 300 are also indicated in FIG. 3A.

FIG. 3B shows a cross-sectional view 308 of anchor 300 in plane B-B of FIG. 3A. A thin circular coil 310, with radius almost as great as the outer radius of anchor 300, is located near the top of anchor 300, i.e. near the proximal end, surrounding the axis of the anchor. In FIG. 3B, coil 310 is only visible as two small cross-sections of the coil, on the left and right sides of the axis of symmetry of the anchor, near the top. Driver slots 304 extend through the center of coil 310. A power source 312, for example a button-shaped battery, is located below slots 304, i.e. distal to slots 304, and an electronics module 314 is located distal to power source 312. Alternatively, as in FIGS. 4A-D, power source 312 is located distal to electronics module 314, or they are located side by side. Hollow region 306 is seen near the bottom of the anchor in FIG. 3B. FIG. 3C shows a cross-sectional view 316 of anchor 300 in plane C-C of FIG. 3A. Four eyelets 318 pass through the wall between slots 304, and are used to attach up to four sutures to the anchor. The two proximal eyelets are nearly at the same level as coil 310, surrounded by coil 310, and the two distal eyelets are well below coil 310, so that sutures would have to pass through the center of coil 310 to go through the distal eyelets. FIG. 3D shows a top view 320 of anchor 300. The circular shape of coil 310 is visible, as are slots 304.

FIG. 3E shows a side perspective view 322 of a suture anchor 324, similar to anchor 300 in FIGS. 3A-3C, with a driver comprising a handle 326, and a driver shaft 328. Two prongs 330 at the end of driver shaft 328 are visible in close-up A. Prongs 330 fit into the two slots 304 of the anchor. The prongs and shaft of the driver are hollow, to accommodate the suture before the anchor is used.

FIG. 4A shows on the right an external perspective view of a suture anchor 400, similar in external appearance to anchor 300 in FIG. 3A. Like anchor 300, anchor 400 has threads 302, driver fitting slots 304, and a hollow space 306. The left side of FIGS. 4A-D shows a cutaway view 402 of anchor 400. Slots 304, coil 310 and eyelets 318 going through the wall separating the two slots are both visible near the top of view 402. Below slots 304 are power source 312 and electronics module 314, but in anchor 400, power source 312 is below (distal to) electronics module 314. Alternatively, power source 312 and/or electronics module 314 are oriented longitudinally, for example side by side, or oriented at another angle. Optionally, power source 312 is a single battery, for example a 1.5 volt silver-oxide battery, or an alkaline battery, or a lithium battery. Although power source 312 is shown in FIG. 4A as a circular button-shaped battery, wider than it is tall, optionally power source 312 is a cylindrical rod shaped battery, taller than it is wide, or equal in length and width, or is a battery in the shape of a rectangular solid. Alternatively, power source 312 comprises two or more batteries, or a different kind of power source such as a supercapacitor, or a combination of a battery and another kind of power source. Optionally, electronics module 314 comprises a printed circuit board (PCB).

The dimensions and number of turns in the coil depends on the diameter of the anchor, on the need to make the coil impedance a good match to the electronics driving it, on the need to make the ohmic losses in the coil low enough so that the power source will last a long time when the EMF generator is producing fields of an intensity useful for therapy, and on the pulse length and pulse repetition frequency that are chosen for good therapeutic effects. For example, suture anchors in bones are typically 4 or 5 mm in diameter, so the outer diameter of the coil might be chosen to be somewhat smaller than that, for example, 3 mm or 3.5 mm or 4 mm or 4.5 mm. Alternatively, if the suture anchor is made somewhat larger than a typical suture anchor, for example with a diameter of 6 mm, 7 mm, or 8 mm, then the outer diameter of the coil could be somewhat greater, for example 5 mm or 6 mm or 7 mm. The radial thickness of the coil, and the length of the coil, may be chosen to be somewhat smaller than the outer radius of the coil, for example 10% or 20% or 30% or 50% of the radius, because adding to the thickness and the length of the coil may not contribute very much to the field produced at a given location, if the additional conductor is too far away longitudinally, or has too small a radius. Once the coil dimensions are chosen, the number of turns in the coil may be chosen so that the coil impedance, at the desired pulse time, matches a typical impedance for an electronic circuit driving the coil, for example a few tens of ohms, which will give currents of a few tens of mA for voltages that are typical of battery voltages, for example 1 to 3 volts. The number of turns is then typically a few hundred or a few thousand, for example 200 turns or 300 turns or 400 turns or 600 turns or 800 turns or 1000 turns or 1300 turns or 1600 turns or 2000 turns, and the number of turns then gives the approximate wire diameter, for example 0.03 mm or 0.05 mm or 0.1 mm or 0.2 mm. A goal for field strength, to have a good therapeutic effect, might be, for example, 2 mT, or 1 mT, or 0.5 mT, or 0.3 mT, or 0.2 mT, or 0.1 mT, on the axis of the coil at a distance of 1 mm, or 2 mm, or 3 mm from the top of the coil in the proximal direction. A pulse length that might produce good therapeutic effects, if the current goes through one cycle of a sine wave for each pulse, might be 20 microseconds or 50 microseconds, or 100 microseconds, or 200 microseconds, corresponding respectively to a frequency of 50 kHz, 20 kHz, 10 kHz, or 5 kHz, and a good choice for the pulse repetition rate might be 10 Hz or 20 Hz or 50 Hz or 100 Hz. Given these coil parameters, a battery may be chosen that provides enough stored energy to keep the EMF generator operating for 1 month, or 3 months, or 6 months, that fits in the space available in the anchor, and that has a typical battery voltage of 1 to 3 volts. Two or more batteries, in parallel or in series, may also be used, to double the voltage or to double the current of one battery. For example, two 337 batteries, each 1.55 volts, may satisfy the design goals.

FIG. 4B shows four suture anchors that may be suitable for combining with an EMF generator, according to an exemplary embodiment of the invention. Anchor design 404 has a suture tied at one end inside the anchor, which makes a loop with the other end of the suture going through the anchor to the other side. The anchor is designed to be driven completely into the bone, for example by pushing or punching or hammering. When the anchor is driven into the bone, the loop remains outside the bone. If an upward pulling force is exerted on the anchor after it is embedded in the bone, for example by pulling on the loop, that causes barbs, located at a bottom (distal) portion of the anchor, to open up, locking the anchor in place. The loop of suture is then placed around the end of the injured soft tissue, for example a torn tendon and drawn tight, attaching the soft tissue to the anchor, and hence to the bone. The upper part of anchor 404 may be narrower than the lower part, allowing the suture to slide freely even between the anchor and the bone, and making it possible for the surgeon to draw the loop tight. Optionally, the coil is incorporated into the upper (proximal) part of anchor 404, above the point where the end of the suture is attached to it. This will allow the coil to generate a relatively larger electromagnetic field directly above the anchor, in the soft tissue, than if the coil were further away, for a given current, and power consumption. The power source and the electronics module need not be near the soft tissue, and are optionally incorporated into anchor 404 lower down, for example below the place where the suture crosses through the anchor to the other side.

Anchor design 406 has screw threads in a bottom (distal) portion, and an upper (proximal) portion with a hexagonal cross-section, and an eyelet for the suture to go through. One or more sutures are threaded through the eyelet, and the anchor can be screwed down into the bone by a conventional hex wrench or screwdriver. In contrast to the anchor shown in FIGS. 3A-3E, it does not have a separate specially designed driver tool attached, during manufacture, to each anchor. Optionally, anchor 406 is driven completely into the bone. Even after the anchor is driven completely into the bone, the sutures may still move freely through the eyelet. During surgery, one or more sutures, previously threaded through the eyelet, are used to suture the soft tissue to the anchor. As with anchor 404, the coil is optionally incorporated into the uppermost part of anchor 406, for example above the eyelet, to bring it close to the soft tissue, while the power source and the electronics module are optionally located further down in anchor 406, below the eyelet.

Anchor design 408 has a proximal tube-shaped portion, on the upper left part of the anchor in the drawing, that surrounds a distal portion, on the lower left part of the anchor in the drawing. One or more sutures, four sutures in the case illustrated in FIG. 4C, pass from the proximal side down into the hollow part of the tube-shaped portion, out the bottom (distal) opening of the tube-shaped portion, and back up in the proximal direction. When the tube-shaped portion is turned relative to the distal portion, for example by a driver tool of some kind inserted into the hollow part of the tube-shaped portion, the tube-shaped portion is forced down around the distal portion, due to a threaded interface between them, trapping the sutures between the tube-shaped portion and the distal portion. Due to threads on the outside the tube-shaped region, turning the tube-shaped portion in this direction also pushes the anchor deeper into the bone. The sutures to the sides of the tube-shaped portion are trapped between the anchor and the surrounding bone helping to hold the anchor in place. In addition, barbs on the sides of the tube-shaped portion are pushed out if a force is exerted on the anchor to pull it away from the bone, for example by pulling on the sutures. These barbs, once deployed, further stabilize the anchor in the bone. As in designs 404 and 406, the coil is optionally put inside the proximal end of anchor 408, where it will be closest to the soft tissue, and the power source and electronics module may be put inside the more distal part of anchor 408.

Anchor design 410 is similar to anchor 406, with distal threaded portion that screws into the bone, and a proximal portion with hexagonal cross-section that can be driven into the bone by a hex wrench, for example. Optionally it is driven completely into the bone. It differs from anchor 406 in that there are two eyelets in the proximal portion, so up to two sutures can go through it. Again, the coil is optionally put inside the proximal end of anchor 410, where it will be closest to the soft tissue, and the power source and electronics module may be put inside the more distal part of anchor 408.

FIG. 4C schematically shows two perspective cutaway views of another anchor design with a coil 310, a power source 312, an electronics module 314, and a hollow space 306, all similar to the corresponding parts in FIGS. 4A-D. View 412 shows half of the top portion of the anchor cut way, and view 414 shows a quarter of the whole anchor cut away. The anchor shown in FIG. 4C differs from and has a potential advantage over the anchors shown in FIGS. 3A-3D and FIG. 4A, in that it can be driven into the bone by an ordinary hex screwdriver. It does not need a separate special driving tool that is sold with every anchor. The top of the anchor has a hexagon-shaped depression 416, that a hex screwdriver can fit inside, to drive it into the bone. On the other hand, the anchor designs shown in FIGS. 3A-3D and FIG. 4A-D have the potential advantage that the coil can be right at the top of the anchor, closer to the soft tissue when it is sutured to the anchor, while in the anchor shown in FIG. 4C, the coil is recessed a short distance away from the top of the anchor, to provide a hexagon-shaped depression for a hex screwdriver to fit into.

A suture is passed through an opening 318 on the top surface of the anchor, to the side of the hexagon-shaped depression, visible only in view 414. The suture then passes down through a narrow passageway in the wall of the anchor, part of which is seen as hole 420 in view 412, going to the side of coil 310, electronics module 314, and power source 312. There are two such passageways side by side, and each passageway is wide enough for two sutures to pass through, so there can be as many as four sutures attached to the anchor. The passageways end at hollow space 306, and the suture, or sutures, emerge into hollow space 306. Each suture then goes through one of four eyelets 422 in a partition that divides hollow space 306. On the other side of the partition, the one or more sutures then go into one or both of two similar passageways that go up the wall of the anchor in the back, from the perspective of views 412 and 414. The sutures emerge at openings 424 of the back passageways, at the top surface of the anchor, visible in view 414.

Optionally, the anchor is sold with the sutures already joined to it in this way, by the manufacturer. The surgeon first drives the anchor into the bone, using an ordinary hex screwdriver for example, and then uses the sutures to suture the soft tissue, such as a torn tendon, to the anchor.

In the anchor shown in FIG. 4C, the sutures pass through passageways inside the outer walls of the anchor, to the sides of the power source, since the power source, a single battery, fills up most of the cross-sectional area of the anchor. In some embodiments of the invention, the power source is comprised by two or more batteries, electrically in parallel and/or in series, and located side by side. In that case, the sutures can be routed between two of the batteries. Alternatively, there is only a single battery filling up most of the cross-sectional area of the anchor, but it has a toroidal or horseshoe-like shape, with an opening in the middle that the sutures can pass through.

In an exemplary embodiment of the invention, as shown in FIG. 4D, a coil 428 is located inside a suture 426, and has a small diameter, for example 0.2 mm or 0.3 mm or 0.4 mm or 0.5 mm or 0.6 mm or 0.8 mm. The coil is optionally located inside the suture in a position which is near the proximal end of the anchor. The coil has, for example, a wire diameter of 0.015 mm, 0.03 mm, 0.05 mm, 0.08 mm, 0.1 mm, 0.2 mm, or 0.5 mm. The coil is an air coil which is wound on a cylindrical flexible tube 430. The coil optionally has 1, 2, 3, 4, or 5 layers. The coil optionally has 50, 100, 200, 400, 800, or 1200 turns. The coil optionally has a length of 0.2 cm, 1 cm, or 1-6 cm.

The coil has two lead wires 432, for example, with or without polarization. The lead wires can start at the same end of the coil. The lead wires can run through the suture from the coil toward the direction of the power source and the electronics module. At a point 434 close to the location of the power source and the electronics module, the lead wires optionally run through the wall of the suture and connect to a terminal which is connected to the power source through the electronics module. The electronics module optionally ensures that the coil is only exposed to the voltage of the power source during pulses, with negligible voltage between the lead wires during the intervals between pulses.

Alternatively, the lead wires run from their location in the suture through a designated tunnel that runs in anchor's body towards the power source and electronics module, and connect to the power source through the electronics module. One lead wire will connect via the electronics module to the positive side of the power source, and the other lead wire via the electronics module to the negative side of the battery.

Optionally, the lead wires are long enough so as to enable movement without tearing away from the electronics module and power supply. Optionally, the lead wires connect to positive and negative terminals outside of a compartment inside the anchor where the power source and electronics module are located, and the terminals are connected to the power source through the electronics module.

In some embodiments of the invention, the coil can generate a magnetic flux of 20-500 uT at a distance of 0.5 mm from the coil edge. The peak current running through the coil is, for example, 17 mA.

FIG. 5 shows a schematic view 500 of a torn tendon 502, tied with a suture 504 to a suture anchor 506, similar to anchor 300 in FIGS. 3A-3D, or anchor 400 in FIG. 4A-D. The suture is tied off with a knot. Anchor 506 is embedded in bone 508, for example screwed in. Although all but the top surface of anchor 506 is optionally covered by bone 508, the entire length of anchor 506 is shown as visible in FIG. 5, with the bone treated as if it were transparent. Tendon 502 is, for example, a rotary cuff tendon, in which case bone 508 would be a humerus. Tendon 502 is adjacent to the proximal end of anchor 506, and optionally the coil generating the EMF in tendon 502 is close to the proximal end of anchor 506, as is the case for anchors 300 and 400.

FIG. 6 shows a schematic cross-sectional view 600 of an anchor 602 embedded in a bone 604, with a circular coil 606 just inside the proximal end of anchor 602. The coil generates magnetic field lines 608 which are shown extending upward and to the sides of the coil 606, into the tendon or other soft tissue that the anchor is sutured to. Since the coil cross-section is small compared to the coil radius, the field that the coil generates is close to the field for an infinitely thin circular loop, except close to the coil where its finite thickness and length are important. The field of a circular loop can be expressed analytically by a well known expression involving elliptic integrals, and an even simpler expression along the axis of the loop. Such analytic expressions can be useful in designing a coil and drive electronics that will produce a given magnetic field in a given location relative to the coil.

Other Devices

Alternatively or additionally, the EMF generator may be separate from an implanted device. For example, the EMF generator may be implanted separate from the device and/or may be removable. Alternatively or additionally and external EMF generator may be used.

In some embodiments portions of an EMF source may be built into an orthopedic implant and/or manufactured together with the implant. Alternatively or additionally, portions of the EMF source may be manufactured separately and/or fitted to an orthopedic implant. For example, in some embodiments of the invention the device is positioned in the right place using pins or magnet or glue or a mechanical system. Alternatively portions of the EMF source may be separate from the implant. Optionally separate portions may remain external to the subject and/or may be implanted separately from the orthopedic implant.

In some embodiments the coil may be built into an orthopedic implant and/or manufactured together with the implant while all the other components of the device will be placed outside the body or next to the skin, and/or will transfer energy by inductance to the coil that will generate the EMF inside the body.

In some embodiments, an EMF source may be used with various orthopedic implants for example including an anchor, a plate, a nail, a prosthetic implant, wires, an Ilizarov external fixation system.

In some embodiments EMF may be used to treat any bone and/or orthopedic condition that is treated with implants.

In some embodiments the EMF at the target site may have an intensity of 0.05-0.5 mT. Optionally the EMF field is pulsed.

In some embodiments EMF may be applied to have one or more the following of effects on the tissue: enhanced proliferation, speeding up healing, improving tissue quality (such as bone density), improving bone to implant contact, preventing and/or treating inflammation, lowering inflammation levels, preventing bone absorption and/or damage, improving scar tissue formation, improving scar tissue quality (e.g. thickness, attachments, elasticity and/or strength), improving connection between different types of tissue (e.g. bone to tendon), reducing the tear prevalence of repaired tendons, encouraging regeneration of tissue.

Resonant Energy-Saving Circuit

In some embodiments of the invention, the electronics module includes a resonant energy-saving circuit, in which most of the electromagnetic field energy of each pulse is stored as electrostatic energy of a capacitor between pulses, and then used to supply the electromagnetic field energy of the next pulse, with very little dissipation of energy during the long interval between pulses, and only a small fraction of the energy lost each time it is transferred from the coil to the capacitor and back again. Such a circuit can make the EMF generator much more energy efficient for generating EMF, allowing the EMF treatment of the tendon to continue for a relatively long time using a power source with a relatively small capacity for energy storage.

FIG. 7 schematically shows a circuit diagram for a portion of such a resonant energy-saving circuit, including a coil 1402 with inductance L, a capacitor 1404 with capacitance C, a terminal 1406 that switches between zero volts and the power source (for example, battery) voltage $V_{cc}$, controlled by the pulse generating circuitry, and a terminal 1408 with a voltage controlled by the pulse generating circuitry. The pulse generating circuitry is not shown in FIG. 7. The changes to the voltage 1408 are shown schematically by terminal 1410, which has a positive operating voltage, for example equal to the battery voltage and terminal 1412, which has a negative operating voltage, for example equal to the battery voltage in magnitude. It should be understood that saying that voltage 1408 is positive or negative means positive or negative relative to terminal 1403, and when voltage 1408 is positive, that means it is connected to the positive side of the battery (voltage $V_{cc}$) and terminal 1403 is connected to the negative side of the battery (voltage 0), while when voltage 1408 is negative, this means that it is connected to the negative side of the battery (voltage 0), while terminal 1403 is connected to the positive side of the battery (voltage $V_{cc}$). Initially, at least once several pulses have been initiated and the circuit has reached a steady state, terminal 1408 is set to the positive operating voltage of terminal 1410, and capacitor 1404 has a positive voltage equal to the operating voltage, and there is zero voltage across coil 1402, and no current flowing in the coil. To initiate a pulse, terminal 1408 is set to the negative operating voltage of terminal 1412. At first, capacitor 1404 remains charged at the same positive operating voltage that it had before, and coil 1402 now has a voltage across it equal to nearly twice the operating voltage, if the positive and negative operating voltages are equal in magnitude. Current starts to flow in the coil, slowly at first, because the back emf of the coil nearly cancels out the voltage across it. In FIG. 8, which schematically shows the current 800 in the coil as a function of time, shown on axis 802, and the voltage 804 across the capacitor as a function of time, the pulse is initiated at time 806. As the current in the coil starts to build up, the capacitor starts to discharge. At time 808, the capacitor has completely discharged, and almost all of its energy has gone into the electromagnetic field energy of the coil, which reaches a maximum current. The current, continuing in the same direction, starts to charge up the capacitor with the opposite polarity. At time 810, the capacitor has charged up to the operating voltage, but with polarity opposite to what it was at time 806, and the current and voltage across the coil has fallen to zero. The interval from time 806 to time 810 is one half of a wave period at the resonant frequency $(LC)^{-1/2}$ to first approximation, ignoring the effects of ohmic losses and any other dissipation. Again ignoring dissipation, the current as a function of time between times 806 and 810 is nearly a sine function, at the resonant frequency. The voltage across the capacitor as a function of time between times 806 and 810 is also nearly a sine function, but 90 degrees out of phase with the current as a function of time.

At time 810, if terminal 1408 remains at the negative operating voltage of terminal 1412, or if terminal 1408 is floated, indicated by "State 3" in FIG. 8A, then no more current will flow in coil 1402, and capacitor 1404 will remain fully charged at the negative operating voltage. This state, between pulses, will persist until terminal 1408 is switched back to having the positive voltage of terminal 1410, which is done at time 812 in FIG. 8. The capacitor will start to discharge again, and the current builds up again in the coil, but this time the current will be in the opposite direction from what it was between time 806 and time 810. The current after time 812 will have the same magnitude as a function of time, though opposite in sign, as it had between times 806 and 810, as the capacitor discharges, building up the electromagnetic field of the coil, and then charges up again with its original positive polarity, recovering field energy from the coil. At time 814, half of a resonant frequency wave period after time 812, the capacitor will again be charged to the operating voltage, with its original positive polarity, and the coil current and voltage will again be zero. The circuit has now returned to its state before time 806, and can remain in this between-pulse state until a new current pulse is initiated by changing the voltage of terminal 1408. Optionally, terminal 1408 is floated until the next pulse is initiated.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

An experiment was conducted with rats to determine the effects of generated pulsed electromagnetic field therapy on tendon-to-bone healing: rotator cuff repair, and to investigate the effect of PEMF exposure on rotator cuff healing using an established rat rotator cuff acute detachment and repair model.

A repaired tendon and a repaired tendon-to-bone interface normally present inferior tissue properties compared to a normal RC tendon, in the absence of PEMF treatment. The newly formed tissue is mostly fibrotic and disorganized, and it reattaches poorly to the bone.

Thirty Wistar rats were used in the study. Under anesthesia, a skin incision was made over the deltoid muscle. The deltoid was gently split to uncover the supraspinatus tendon. The tendon was then cut adjacent to its footprint on the humeral head, and its footprint was gently debrided with a scalpel to enhance bone-to-tendon healing. and reattached to the humeral head by suturing to the humerus, the suture going through a hole through the hone that had been created with a sharp needle. In test locations (RCHA group), which were the right shoulder of each rat, pulsed EMF was applied using an implanted EMF source, the Rotator Cuff Healing Anchor (RCHA), which was sutured in a subcutaneous space directly over the seam line between the reattached tendon and the humeral head. The RCHA was the dental implant device described in U.S. Pat. No. 10,376,708 to Neuman et al. In control locations (cntrl group), which were the left shoulder of each rat, pulsed EMF was not applied. At 3 weeks and again at 6 weeks, 10 rats were sacrificed for biomechanical testing and micro-CT scans, and histology studies were done on 5 rats each time, comparing the results for the right shoulders (RCHA group) and left shoulders (control group).

Results are illustrated in FIGS. 9 through 18. The scale of FIGS. 13-14 ranges from normal 0 to very abnormal 3.

The results imply that applying a pulsed EMF has a positive effect on early rotator cuff healing in rats. Specifically, improved biomechanical elasticity parameters and better collagen organization were found in the RCHA treated group as compared to the controls.

The results also imply that applying a pulsed EMF improved collagen I expression. Importantly, no adverse effects were identified in any mechanical, histological or bone property. Pulsed EMF exposure appeared to improve early tendon-to-bone healing in an acute rat supraspinatus detachment and repair model supporting the use in a clinical scenario of rotator cuff healing for other animals including humans.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. An anchoring system, comprising an anchor and a suture, for attaching injured soft tissue to a bone and generating a therapeutic electromagnetic field at least in a part of the soft tissue when the soft tissue is sutured to the anchor with the suture, the system comprising:
   a) a coil, encased inside the anchor, that generates the electromagnetic field when a current runs through it;
   b) an electronics module in the anchor that controls the current in the coil; and
   c) an electric power source in the anchor that provides electric power to the electronics module and the coil;
wherein the suture is attached to the anchor, and wherein the anchor is configured for affixing the anchoring system to the bone.

2. An anchoring system according to claim 1, wherein the anchor is threaded, and affixes the anchoring system to the bone by screwing into the bone.

3. An anchoring system according to claim 2, comprising a fitting in the anchor into which or around which a driving tool can be inserted, to screw the anchor into the bone.

4. An anchoring system according to claim 1, comprising one or more eyelets in the anchor for attaching the suture to the anchor.

5. An anchoring system according to claim 1, the anchor configured to attach to the bone by penetrating at least partly into the bone in an axial direction of the anchor.

6. An anchoring system according to claim 5, wherein the coil is comprised in the anchor, and most of a conductor volume of the coil is located within 2 mm in the axial direction of a proximal end of the anchor.

7. An anchoring system according to claim 5, wherein the coil is comprised in the anchor, and a proximal part of the anchor has a substantially circular cross-sectional area, aside from any threads for screwing it into the bone, and the coil extends over an area perpendicular to the axial direction that is at least 50% of the circular cross-sectional area of the proximal part of the anchor.

8. Anchoring system according to claim 5, wherein the coil is comprised in the anchor, and the coil, when it has current running in it, has a direction of magnetic moment oriented within 20 degrees of the axial direction.

9. An anchoring system according to claim 8, wherein the coil is comprised in the anchor, and an effective length of the coil, defined as twice a standard deviation of a distribution of conductor along the direction of magnetic moment, is less than an effective diameter, defined as a maximum extent of conductor in a direction perpendicular to the direction of the magnetic moment.

10. An anchoring system according to claim 5, wherein the coil is comprised in the anchor, and the electronics module is configured to cause enough current to pass through the coil to produce a magnetic field of at least 0.05 millitesla, in at least one location at least 1 mm in an axial direction beyond a proximal end of the anchor.

11. An anchoring system according to claim 5, wherein the coil is comprised in the anchor, the anchor comprising one or more eyelets for attaching the suture to the anchor, at least one eyelet located distal to the coil, or passing through the coil.

12. An anchoring system according to claim 1, wherein the electronics module is configured to cause the current to run through the coil, for a series of pulse times shorter than 300 microseconds, with a waiting period following each pulse time that is at least 100 times longer than the pulse time, with the current during the waiting period sufficiently low so that the total energy dissipated by the current during the waiting time is less than the total energy dissipated by the current during the pulse time.

13. An anchoring system according to claim 12, wherein the electronics module is configured to cause the current running through the coil during each pulse time to be substantially one cycle of a sine wave.

14. An anchoring system according to claim 12, wherein the electronics module comprises a capacitor, and the electronics module is configured to cause most of the maximum electromagnetic field energy of the coil during each pulse time to go to electric field energy of the capacitor and to remain there during the following waiting period, and to return back to electromagnetic field energy of the coil during the next pulse time.

15. An anchoring system according to claim 1, wherein the electric power source comprises one or more batteries.

16. An anchoring system according to claim 1, wherein the coil, the electronics module and the electric power source are sealed inside the anchor.

17. An anchoring system according to claim 1, wherein the suture passes from an opening in a proximal surface of the anchor, between two or more batteries or through a hole in one battery, through an eyelet distal to the battery or batteries, back between two or more batteries or through a hole in one battery, and back through an opening in the proximal surface of the anchor.

18. A method of using the anchor system of claim 1 for treating a patient with an injured soft tissue, comprising:
   a) affixing the anchor to a bone of the patient;
   b) suturing the soft tissue to the anchor with the suture; and
   c) using the coil to generate therapeutic electromagnetic fields at least in a part of the soft tissue adjacent to the anchor for at least one day.

19. A method according to claim 18, comprising:
   a) continuing to generate the electromagnetic fields for a period of time and then stopping; and
   b) leaving the anchor inside the patient's body for at least a year after stopping.

20. A method according to claim 18, wherein affixing the suture anchor to the bone comprises screwing the anchor into the bone using a driving tool inserted into a fitting in the anchor.

21. A method according to claim 18, wherein affixing the suture anchor to the bone comprises punching the anchor into the bone.

22. A method according to claim 18, comprising using the coil to generate pulsed therapeutic electromagnetic fields in the soft tissue, with waiting times between the pulses that are at least 100 times as long as the pulses.

23. A method according to claim 22, wherein the electromagnetic field during each pulse is substantially a sawtooth wave.

24. A method according to claim 23, wherein the electromagnetic field during each pulse is substantially one cycle of a sine wave.

25. A method according to claim 24, wherein generating the pulsed electromagnetic field comprises:
   a) recovering most of the electromagnetic field energy from each pulse and storing it in a capacitor encased in the anchor; and
   b) using most of the stored energy to generate the next pulse.

26. A method according to claim 23, wherein the peak magnetic field within each pulse is at least 0.2 mT everywhere within 1 mm of a proximal end of the anchor in the proximal direction, and within 2 mm of a longitudinal axis of the anchor.

27. An anchoring system according to claim 1, wherein the anchor is configured to attach to the bone by being driven completely into the bone in an axial direction of the anchor, so all but a top surface of the anchor is covered by bone.

28. An anchoring system according to claim 1, wherein the anchor is a suture anchor.

29. An anchoring system according to claim 1, wherein the anchor is uniform in width, aside from any screw threads, so that it can be driven completely into the bone.

30. An anchor for attaching injured soft tissue to a bone and generating a therapeutic electromagnetic field at least in a part of the soft tissue when the soft tissue is sutured to the anchor, the anchor comprising:
   a) an affixing portion configured for affixing the anchor to the bone;
   b) a coil encased inside the anchor that generates the electromagnetic field when a current runs through it;
   c) an electronics module that controls the current in the coil;

d) an electric power source the provides electric power to the electronics module and the coil; and e) one or more eyelets for attaching a suture to the anchor.

31. An anchoring system, comprising an anchor and a suture, for attaching injured soft tissue to a bone and generating a therapeutic electromagnetic field at least in a part of the soft tissue when the soft tissue is sutured to the anchor with the suture and the anchor is embedded in the bone, the system comprising:

a) a coil that generates the electromagnetic field when a current runs through it;

b) an electronics module in the anchor that controls the current in the coil; and c) an electric power source in the anchor that provides electric power to the electronics module and the coil; wherein the suture is attached to the anchor, and wherein the anchor is configured for affixing the anchoring system to the bone with the coil beneath the bone's surface.

\*  \*  \*  \*  \*